United States Patent
Masko et al.

(10) Patent No.: US 11,116,973 B1
(45) Date of Patent: Sep. 14, 2021

(54) SYSTEM AND METHOD FOR A MEDICAL DEVICE

(71) Applicant: i-Lumen Scientific, Inc., Bloomington, MN (US)

(72) Inventors: Marshall T. Masko, Minnetonka, MN (US); John C. Velure, Minnetonka, MN (US); Thu-Ha Duncan, Cleveland, TN (US); Alexander B. Lemaire, Edina, MN (US); Charles A. Lemaire, Apple Valley, MN (US)

(73) Assignee: i-Lumen Scientific, Inc., Bloomington, MN (US)

( * ) Notice: Subject to any disclaimer, the term of this patent is extended or adjusted under 35 U.S.C. 154(b) by 0 days.

(21) Appl. No.: 17/180,669

(22) Filed: Feb. 19, 2021

Related U.S. Application Data

(62) Division of application No. 29/754,410, filed on Oct. 9, 2020.

(51) Int. Cl.
   *A61N 1/36* (2006.01)
   *A61N 1/04* (2006.01)

(52) U.S. Cl.
   CPC ......... *A61N 1/36046* (2013.01); *A61N 1/048* (2013.01); *A61N 1/0476* (2013.01)

(58) Field of Classification Search
   CPC ... A61N 1/36046; A61N 1/048; A61N 1/0476
   See application file for complete search history.

(56) References Cited

U.S. PATENT DOCUMENTS

| | | |
|---|---|---|
| 4,018,218 A | 4/1977 | Carlson et al. |
| 5,522,864 A | 6/1996 | Wallace et al. |
| 6,035,236 A | 3/2000 | Jarding et al. |
| 6,275,735 B1 | 8/2001 | Jarding et al. |
| 6,445,955 B1 | 9/2002 | Michelson et al. |
| 6,636,754 B1 | 10/2003 | Baura et al. |
| 7,062,319 B1 | 6/2006 | Ihme et al. |
| 7,158,834 B2 | 1/2007 | Paul, Jr. |
| 7,215,989 B1 | 5/2007 | Burks |
| 7,326,181 B2 | 2/2008 | Katims |
| 8,116,841 B2 | 2/2012 | Bly et al. |
| 8,731,657 B1 | 5/2014 | Shambayati et al. |
| 9,283,371 B2 | 3/2016 | Duncan |
| 10,391,312 B2 | 8/2019 | Mowery et al. |
| 2005/0137649 A1 | 6/2005 | Paul, Jr. |
| 2008/0171929 A1 | 7/2008 | Katims |
| 2013/0172829 A1* | 7/2013 | Badawi ................ A61F 9/0008 604/294 |
| 2016/0287173 A1* | 10/2016 | Abreu ..................... G02C 11/10 |
| 2018/0318586 A1* | 11/2018 | Salazar .............. A61N 1/36046 |

(Continued)

FOREIGN PATENT DOCUMENTS

| WO | WO_2020131329 | 6/2020 |
|---|---|---|
| WO | WO_2020132337 | 6/2020 |

*Primary Examiner* — Eugene T Wu
(74) *Attorney, Agent, or Firm* — Charles A. Lemaire; Jonathan M. Rixen; Lemaire Patent Law Firm, P.L.L.C.

(57) ABSTRACT

A cable-holder system for physically supporting connections to a medical device used on a patient, the system including a first portion configured to be supported at the patient's head; a second portion moveably coupled to the first portion; and an electrical connector configured to electrically connect to the medical device, wherein the electrical connector is physically connected to the second portion.

20 Claims, 27 Drawing Sheets

(56) References Cited

U.S. PATENT DOCUMENTS

2019/0143116 A1* 5/2019 Mowery ............ A61N 1/36034
607/53
2020/0171307 A1* 6/2020 Rockley ............... A61N 1/0484

* cited by examiner

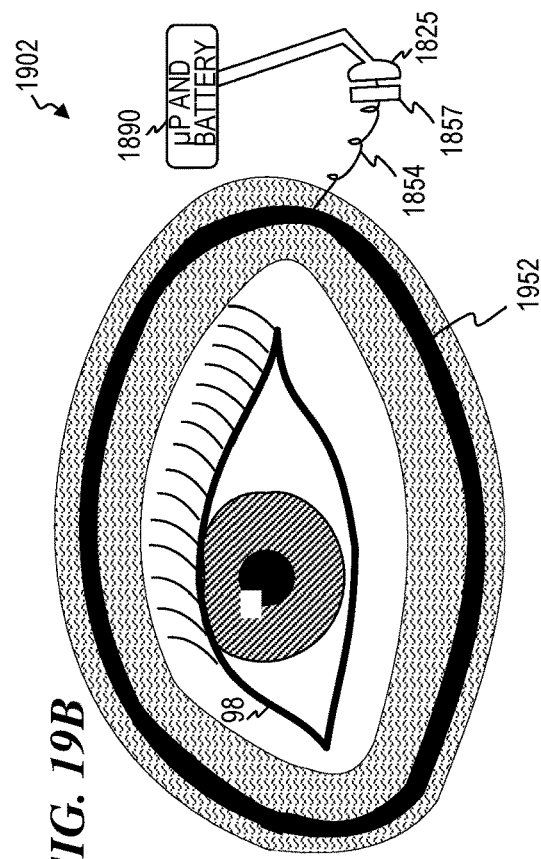
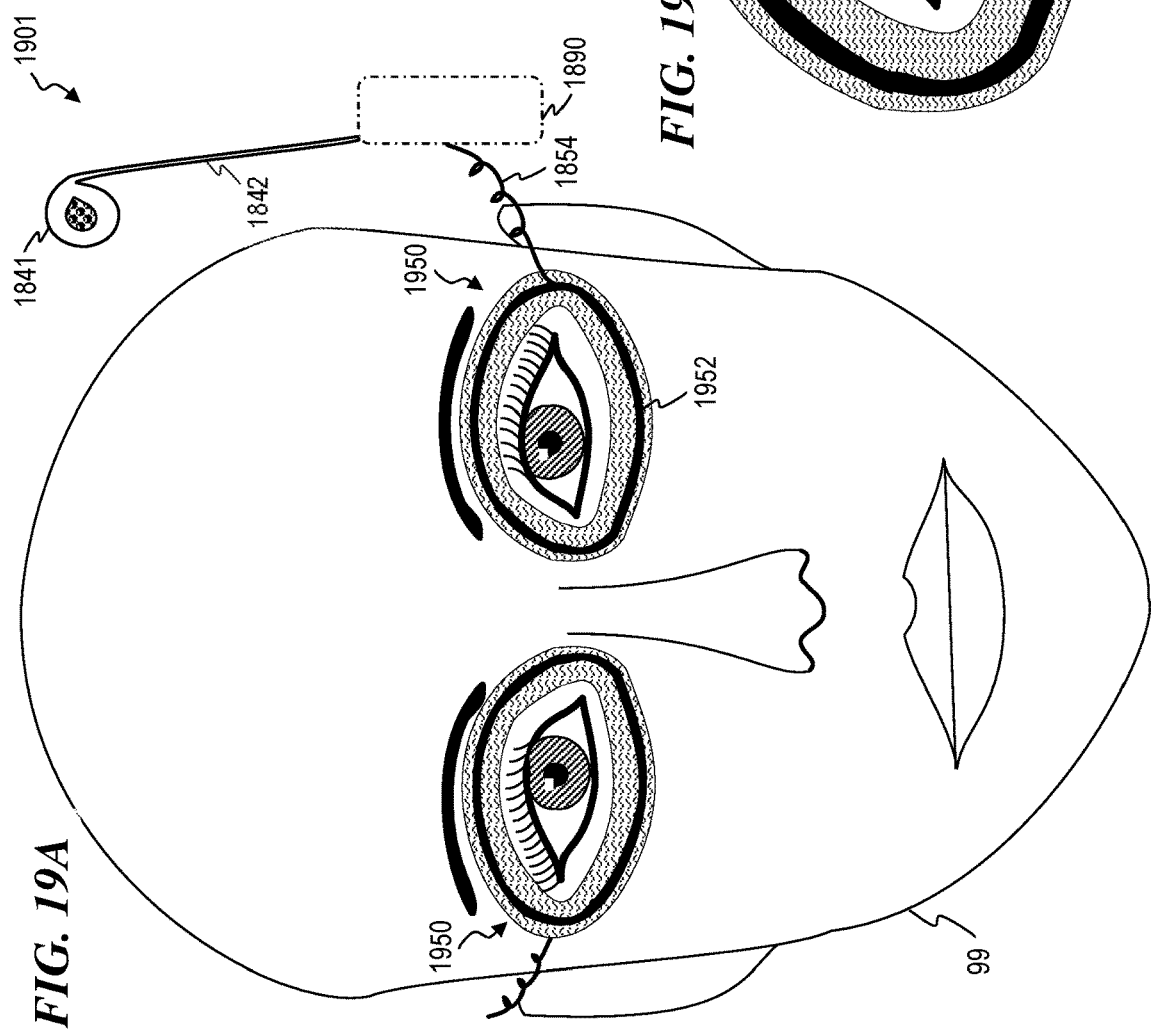
FIG. 19A
FIG. 19B

SYSTEM AND METHOD FOR A MEDICAL DEVICE

CROSS-REFERENCE TO RELATED APPLICATIONS

This application is a divisional application of U.S. Design Pat. application No. 29/754,410 filed Oct. 9, 2020, which is incorporated herein by reference in its entirety.

This application is related to:

U.S. Pat. No. 10,391,312, issued Aug. 27, 2019 to Blair P. Mowery et al. and titled "APPARATUS AND METHOD FOR OCULAR MICROCURRENT STIMULATION THERAPY";

PCT Application Serial Number PCT/US2016/051550 filed on Sep. 13, 2016 with the title "APPARATUS AND METHOD FOR OCULAR MICROCURRENT STIMULATION THERAPY" (published as WO 2017/048731);

PCT Application Serial Number PCT/US2019/063404 filed on Nov. 26, 2019, by Marshall T. Masko et al., titled "APPARATUS AND METHOD FOR MICROCURRENT STIMULATION THERAPY" (published as WO 2020/131329);

PCT Application Serial Number PCT/US2019/067627 filed on Dec. 19, 2019, by Marshall T. Masko et al., titled "MICROCURRENT-STIMULATION-THERAPY APPARATUS AND METHOD" (published as WO 2020/132337);

PCT Application Serial Number PCT/US2020/021267 filed on Mar. 5, 2020, by Marshall T. Masko et al., titled "VISION TESTING AND TREATMENT SYSTEM AND METHOD";

U.S. Provisional Patent Application No. 62/283,870, filed Sep. 15, 2015 by Mowery et al., titled "APPLIANCE FOR MICROCURRENT STIMULATION THERAPY USING A DISPOSABLE MATERIAL AFIXED TO THE UPPER AND LOWER EYE LID & OTHER BODY PARTS";

U.S. Provisional Patent Application No. 62/283,871, filed Sep. 15, 2015 by Masko et al., titled "APPARATUS FOR A METHOD OF APPLICATION OF MICROCURRENT STIMULATION THERAPY, CONSISTING OF A GOGGLE DEVICE AFFIXED TO & ENCIRCLING THE UPPER AND/OR LOWER EYELIDS, AS WELL AS OTHER BODY PARTS";

U.S. Provisional Patent Application No. 62/365,838, filed Jul. 22, 2016 by Tapp et al., titled "APPLIANCE FOR MICRO-CURRENT STIMULATION";

U.S. Provisional Patent Application 62/783,116 filed on Dec. 20, 2018, by Masko et al., titled "APPARATUS AND METHOD FOR MICROCURRENT STIMULATION THERAPY";

U.S. Provisional Patent Application 63/025,987 filed on May 15, 2020, by Duncan et al., titled "ELECTRODE SYSTEM FOR VISION TREATMENT AND METHOD"; each of which is incorporated herein by reference in its entirety.

BACKGROUND

U.S. Pat. No. 4,018,218 to Carlson et al. issued on Apr. 19, 1977 with the title "Method and apparatus for sleep induction," and is incorporated herein by reference. U.S. Pat. No. 4,018,218 describes an apparatus and method to induce sleep in a patient that utilizes an oscillator to control the frequency of electric impulses received by the patient. First and second multivibrators generate the signals necessary to stimulate the central nervous system by conduction through the optic nerve tract, and also to generate a visual aura caused by stimulation of the retina of the eye. An amplifier amplifies the signals generated by the multivibrators and electrodes transmit the amplified signal to the patient. The various components of the apparatus may be stored in an eye frame structure wherein eye lid electrode pads are held in place contiguous the eyes of the patient, and wherein mastoid electrode pads are held in place by means of the frame ear hooks.

U.S. Pat. No. 5,522,864 to Wallace et al. issued on Jun. 4, 1996 with the title "Apparatus and method for ocular treatment," and is incorporated herein by reference. U.S. Pat. No. 5,522,864 describes that macular degeneration and other ocular pathology in a subject are treated by the steps of: placing a positive electrode of a direct current source in electrical contact with a closed eyelid of a subject; placing a negative electrode of the source in electrical contact with the posterior neck of the subject; and causing a constant direct current of 200 µA to flow between the electrodes through the subject for about 10 minutes. The source can be a portable, battery powered constant direct current generator which is affixed to the subject. The subject can ambulate during treatment.

U.S. Pat. No. 6,035,236 issued to Jarding, et al. on Mar. 7, 2000 with the title "Methods and apparatus for electrical microcurrent stimulation therapy," and is incorporated herein by reference. U.S. Pat. No. 6,035,236 describes an apparatus for supplying an electrical signal to a body part in order to provide microcurrent stimulation therapy to the body part. The apparatus preferably comprises a first sweep wave or sweep frequency signal generator configured to generate a first sweep wave signal, a buffer amplifier circuit configured to receive the first sweep wave signal from the first sweep signal generator and amplify and buffer the sweep wave signal creating a buffered sweep wave signal. In addition, the apparatus preferably includes a current limiting circuit configured to receive the buffered sweep wave signal from the buffer amplifier circuit and limit the amount of current supplied to the body part. Finally, the apparatus preferably comprises a probe for applying the sweep wave signal to the body part. The apparatus may further comprise a second signal generator for generating a second signal which may comprise either a sweep wave signal or a non-sweep wave signal. The apparatus also will include a signal combining circuit configured to receive the first and second signals from the first and second signal generators and combine the first and second signals into a composite sweep wave signal.

U.S. Pat. No. 6,275,735 issued to Jarding, et al. on Aug. 14, 2001 with the title "Methods and apparatus for electrical microcurrent stimulation therapy," and is incorporated herein by reference. U.S. Pat. No. 6,275,735 describes a method and apparatus for providing microcurrent stimulation therapy to a body part is disclosed. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

U.S. Pat. No. 6,445,955 to Michelson et al. issued on Sep. 3, 2002 with the title "Miniature wireless transcutaneous electrical neuro or muscular-stimulation unit," and is incorporated herein by reference. U.S. Pat. No. 6,445,955 describes a miniature wireless transcutaneous electrical neuro or muscular stimulation unit. The unit has a housing attached to a plurality of electrodes. An electronics module containing an electrical circuit is contained within the housing and provides a sequence of monophasic or biphasic pulses to a patient's pain site via the electrodes. The electrodes can be disposable and come in a variety of shapes and sizes. The patient may select and control the intensity and the frequency of the pulses by choosing one of several TENS and microcurrent waveforms, as well as the orientation and quantity of the electrodes. The means for supplying power to the electronics module can be integrated with the electrodes in one detachable and disposable assembly. A worn-remote controller can send transmission signals to a receiver within the electronic module thereby allowing the patient to program specific units placed on the patient's body to perform operations in a specified series of waveforms. The electrodes may be embedded in a splint, bandage, brace or cast, where wires or flex-circuit material connect the electrodes to the unit. The electrodes can be arranged in a grid-like manner to allow for programming of a specific firing order which provides for greater therapeutic effect to a pain site, and may also be embedded in adhesive strips, similar to a conventional Band-Aid.

U.S. Pat. No. 6,636,754 issued to B aura et al. on Oct. 21, 2003 with the title "Apparatus and method for determining cardiac output in a living subject," and is incorporated herein by reference. U.S. Pat. No. 6,636,754 describes an improved apparatus and method for determining the cardiac output of a living subject. Their improved apparatus generally comprises one or more electrode assemblies or patches affixed to the skin of the subject in the vicinity of the thoracic cavity. The terminals of each electrode patch are in contact with an electrolytic gel, and are spaced a predetermined distance from one another within the patch. This predetermined spacing allows for more consistent measurements, and also allows for the detection of a loss of electrical continuity between the terminals of the patch and their associated electrical connectors in the clinical environment. The method generally comprises generating and passing a stimulation current through the terminals and the thoracic cavity of the subject, and measuring the impedance as a function of time. This impedance is used to determine cardiac muscle stroke volume, which is then used in conjunction with the subject's cardiac rate (also detected via the electrode patches) to determine cardiac output. A method of detecting a loss of electrical continuity in one or more of the terminals of the electrode patch is also disclosed.

U.S. Pat. No. 7,062,319 issued to Ihme, et al. on Jun. 13, 2006 with the title "Method and arrangement for determining suitable treatment frequency and/or intensity," and is incorporated herein by reference. U.S. Pat. No. 7,062,319 describes a method and arrangement for determining a suitable treatment frequency and/or intensity of a treatment signal used in electrical treatment. In the method, a stimulating electrical signal is directed to an object to produce different reaction types in the object at different intensities of the stimulating electrical signal. For at least three different reaction types, the intensity of the stimulating electrical signal at which a reaction type occurred is stored. The electrical signal intensities stored for the different reaction types at least at three different frequencies are compared with reference values and the frequency and/or signal intensity at which the signal intensity deviates sufficiently from one or more reference values is determined. The method utilizes the frequency and/or signal intensity found in the process in determining the suitable treatment frequency and/or signal intensity.

U.S. Pat. No. 7,158,834 issued to Paul, Jr. on Jan. 2, 2007 with the title "Method and apparatus for performing microcurrent stimulation (MSC) therapy," and is incorporated herein by reference. U.S. Pat. No. 7,158,834 describes a method and apparatus for providing microcurrent stimulation (MSC) therapy. U.S. Pat. No. 7,158,834 states: it has been determined that the application of microcurrent signals at particular frequencies to the eye for particular periods of time stabilizes and even improves conditions of macular degeneration and other ocular diseases.

U.S. Pat. No. 7,215,989 issued to Burks on May 8, 2007 with the title "Multiple electrode assembly," and is incorporated herein by reference. U.S. Pat. No. 7,215,989 describes multiple electrode assemblies that provide an electrical connection between a patient's body and monitoring equipment. A multiple electrode assembly requires only half as many assemblies as a conventional single electrode assembly to attach a patient to multiple pieces of equipment. Less time is required to attach the patient to the monitoring equipment. There is less patient discomfort since fewer assemblies are attached to the patient. The placement of fewer assemblies also leads to a reduced cost. The assemblies can take on a number of different shapes and lead attachment configurations to accommodate a wide range of monitoring functions.

U.S. Pat. No. 7,326,181 issued to Katims on Feb. 5, 2008 with the title "Nervous tissue stimulation device and method," and is incorporated herein by reference. U.S. Pat. No. 7,326,181 describes a method using a precisely controlled, computer programmable stimulus for neuroselective tissue stimulation that does not leave a sufficient voltage or electrical artifact on the tissue being stimulated that would interfere or prevent a monitoring system from recording the physiological response is utilized to evaluate the physiological conduction of the tissue being studied. A computer controls both the waveform, duration and intensity of the stimulus. An output trigger to the nerve response recording component controls the timing of its operation. A neuroselective nervous tissue response latency and amplitude may be determined. The computer controlled stimulus may also be administered for therapeutic purposes.

U.S. Pat. No. 8,116,841 issued to Bly, et al. on Feb. 14, 2012 with the title "Adherent device with multiple physiological sensors," and is incorporated herein by reference. U.S. Pat. No. 8,116,841 describes an adherent device to monitor a patient for an extended period comprises a breathable tape. The breathable tape comprises a porous material with an adhesive coating to adhere the breathable tape to a skin of the patient. At least one electrode is affixed to the breathable tape and capable of electrically coupling to a skin of the patient. A printed circuit board is connected to the breathable tape to support the printed circuit board with the breathable tape when the tape is adhered to the patient. Electronic components electrically are connected to the printed circuit board and coupled to the at least one electrode to measure physiologic signals of the patient. A breathable cover and/or an electronics housing is disposed over the circuit board and electronic components and connected to at least one of the electronics components, the printed circuit board or the breathable tape.

U.S. Pat. No. 8,731,657 issued to Shambayati, et al. on May 20, 2014 with the title "Multi-mode microcurrent stimulus system with safety circuitry and related methods," and is incorporated herein by reference. U.S. Pat. No. 8,731,657 describes a microcurrent stimulation device with a power supply, two or more electrodes electronically coupled to the power supply, a microcontroller configured to generate an electromagnetic waveform, an impedance measurement module configured to measure electrical impedance of one or more biological tissues between the two or more electrodes. A first safety circuit monitors electric current flow through one or more components of the microcurrent stimulation device and interrupts electric current flow if the electric current flow through the one or more components is above a predetermined level. A second safety circuit interrupts electric current flow through the one or more components if a firmware failure occurs.

U.S. Pat. No. 9,283,371 issued to Thu-Ha Duncan on Mar. 15, 2016 with the title "Electro-stimulation system" which is incorporated herein by reference. U.S. Pat. No. 9,283,371 describes an electro-stimulation system with a compact power and control assembly and a plurality of shaped gel electrode patches with instructions to facilitate user administration of therapy.

U.S. Patent Publication 2005/0137649 by Paul, Jr. published on Jun. 23, 2005 with the title "Method and apparatus for performing microcurrent stimulation (MSC) therapy," and is incorporated herein by reference. Patent Publication 2005/0137649 describes a method and apparatus for providing microcurrent stimulation (MSC) therapy, and asserted: it has been determined that the application of microcurrent signals at particular frequencies to the eye for particular periods of time stabilizes and even improves conditions of macular degeneration and other ocular diseases and that experimental data from clinical trials shows that results of persons who underwent therapy are at least better than placebo, and that the therapy is safe and efficacious. Patent Publication 2005/0137649 continued: experimental data from clinical trials showed that approximately 98% of the patients who underwent the MCS therapy of the invention experienced either stabilization or improvement of macular degeneration within one year of starting therapy. Of this percentage, approximately 65% of the patients subjected to the MCS therapy experienced improved vision, while approximately 32% experienced stabilization of macular degeneration (i.e., no further loss of vision).

U.S. Patent Publication 2008/0171929 by Katims published on Jul. 17, 2008 with the title "Method for standardizing spacing between electrodes, and medical tape electrodes," and is incorporated herein by reference. Patent Publication 2008/0171929 describes Standardization between paired electrodes is maintained in a medical device without needing a Mylar spreader, such as by forming the paired electrodes integrally with a tape part.

BRIEF DESCRIPTION OF THE DRAWINGS

FIG. 16A-1 is a perspective view of a cable-holder system 1601, according to some embodiments of the present invention.
FIG. 16A-2 is a perspective view of a cable-holder system 1601 showing moveable portion 1620 rotated such that electrical connection 1627 is fully extended away from system 1601, according to some embodiments of the present invention.
FIG. 19A is a schematic front-view diagram of a therapy-appliance system 1901 having two substrates 1950 positioned around the left and right eyes, respectively, of a person 99, according to some embodiments of the present invention.
FIG. 19B is a front view of a system 1902 showing a therapy-appliance substrate 1950 positioned around a person's eye 98, according to some embodiments of the present invention.

DETAILED DESCRIPTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1:
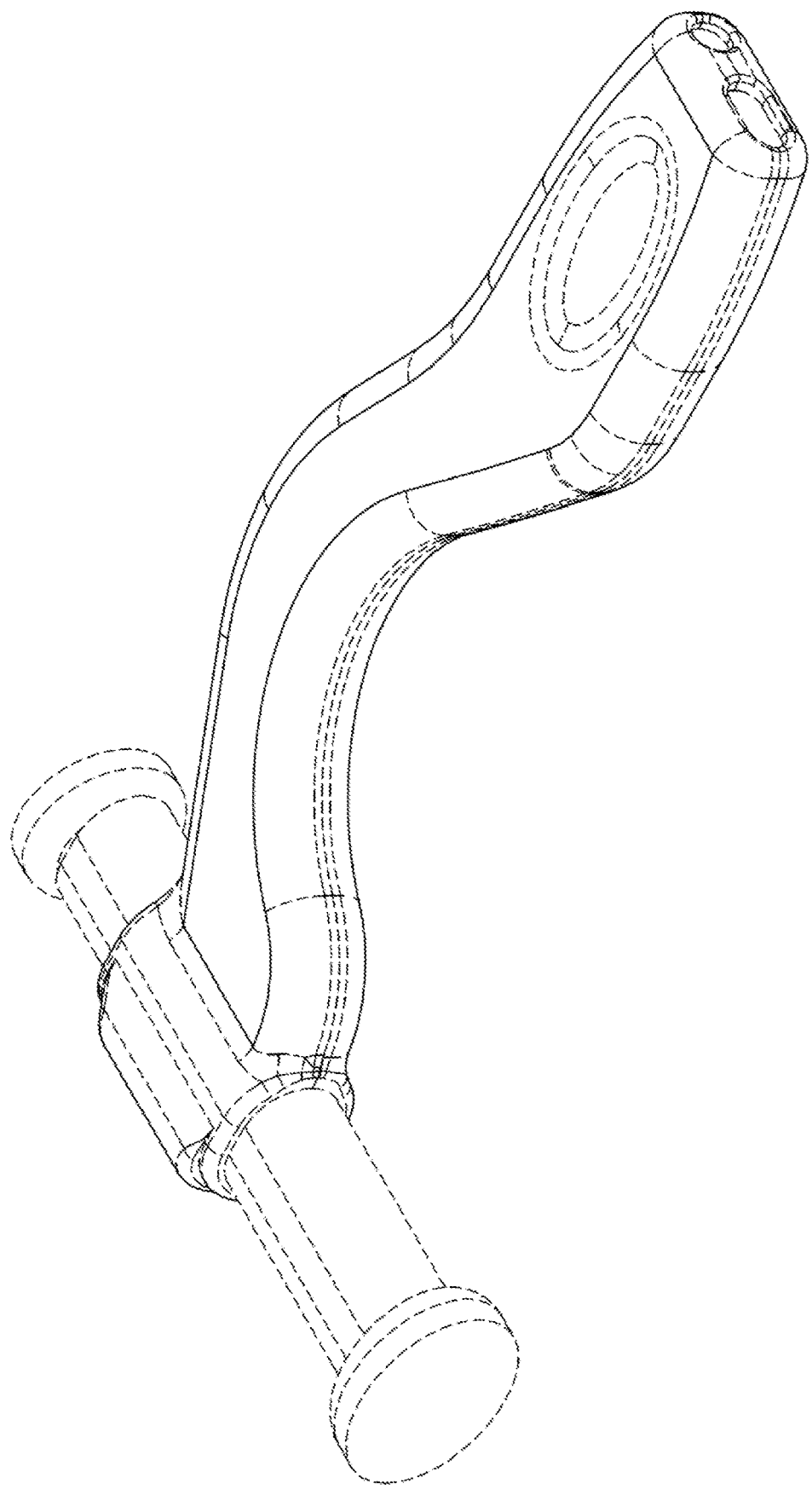
FIG. 1 is a perspective view of a decorative medical device.

FIG. 1 is a perspective view of a decorative medical device.

Figure 2:
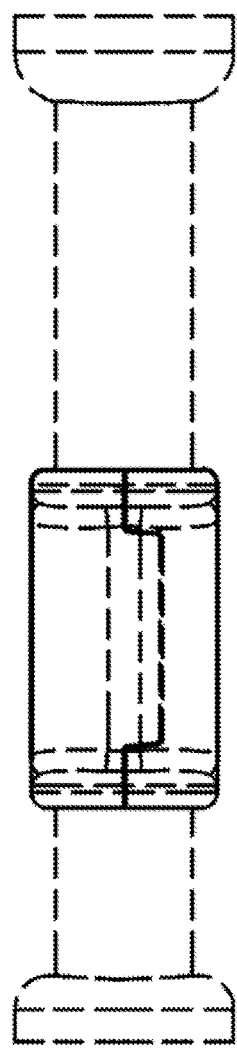
FIG. 2 is a top view thereof.

FIG. 2 is a top view of the decorative medical device.

Figure 3:
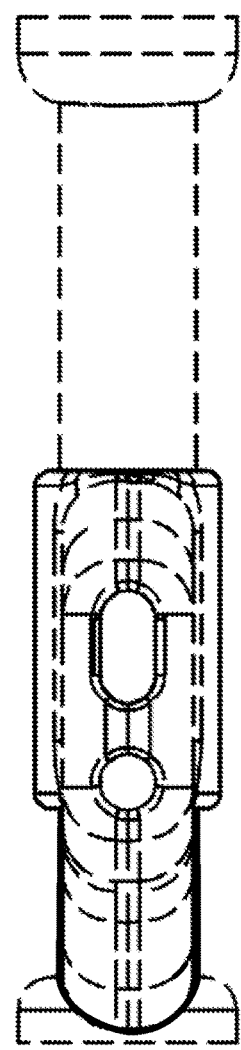
FIG. 3 is a bottom view thereof.

FIG. 3 is a bottom view of the decorative medical device.

Figure 4:
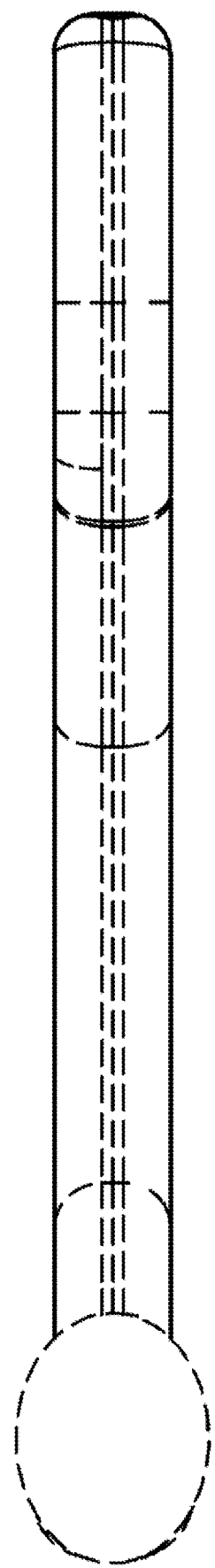
FIG. 4 is a left-side view thereof.

FIG. 4 is a left-side view of the decorative medical device.

Figure 5:
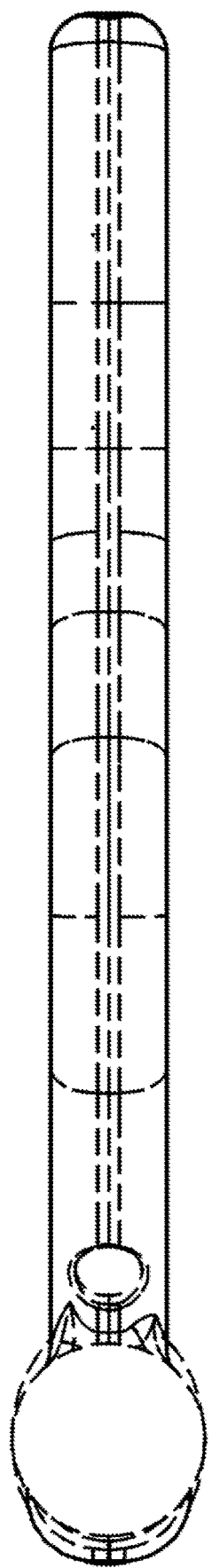
FIG. 5 is a right-side view thereof.

FIG. 5 is a right-side view of the decorative medical device.

Figure 6:
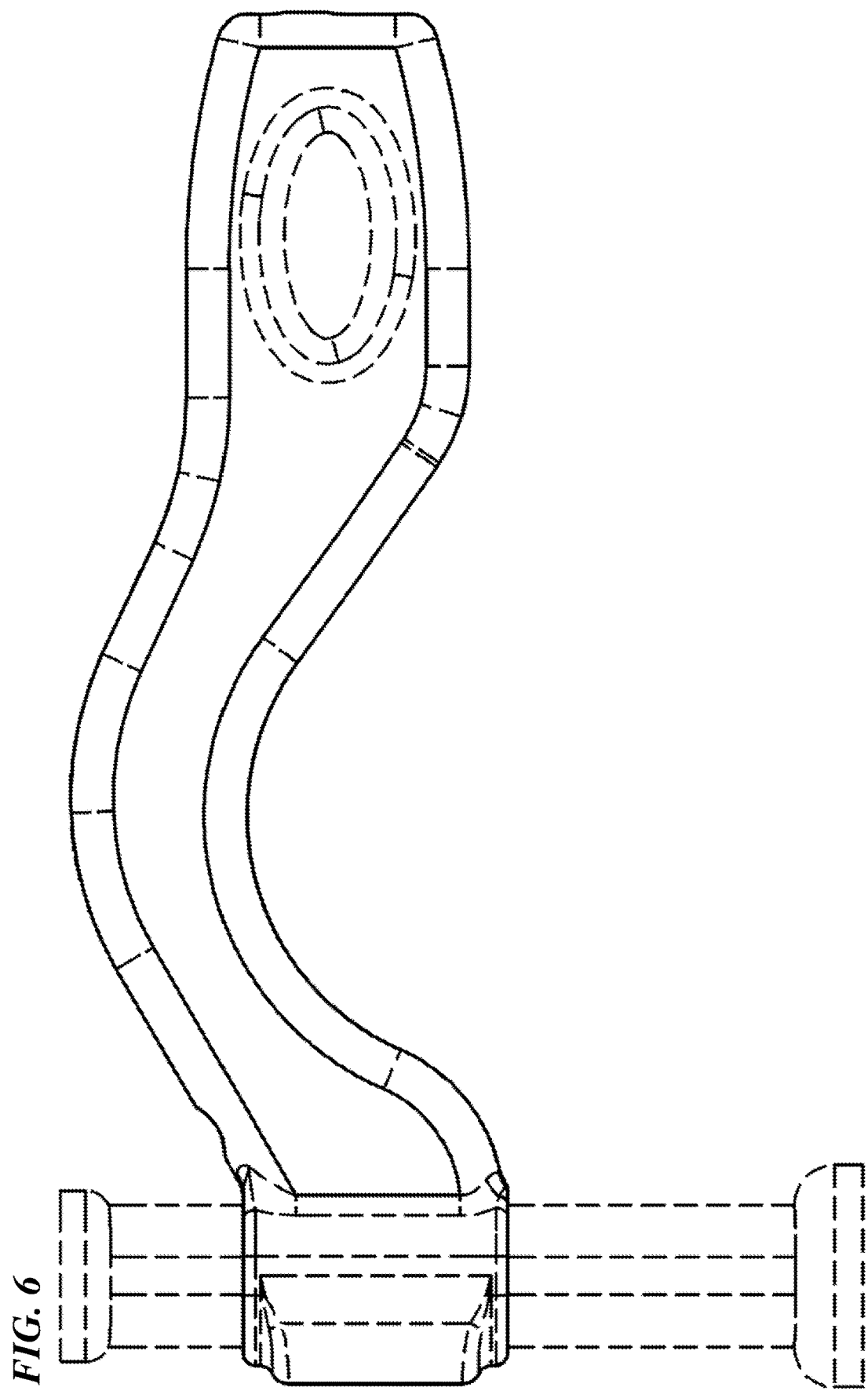
FIG. 6 is a front view thereof.

FIG. 6 is a front view of the decorative medical device.

Figure 7:
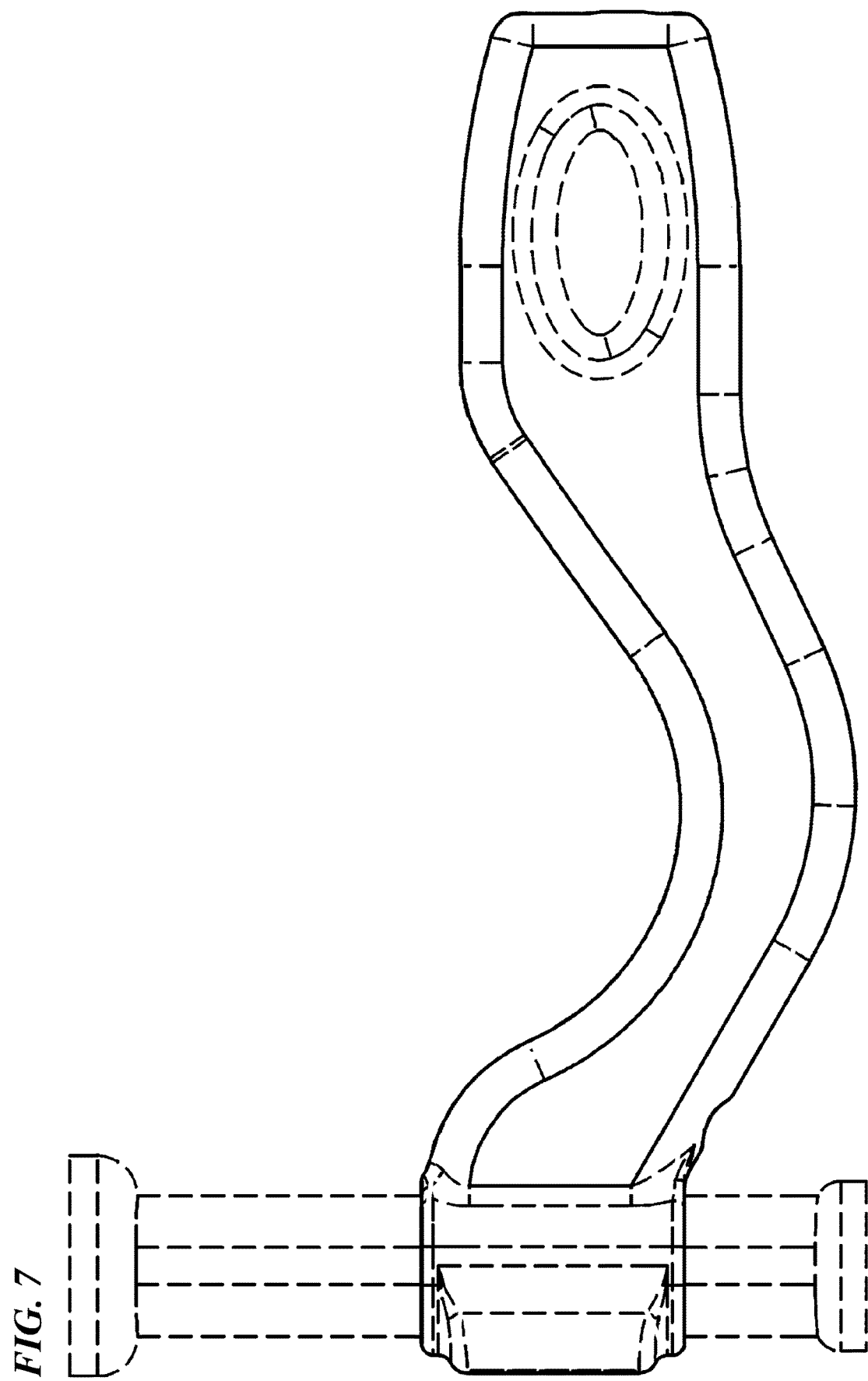
FIG. 7 is a back view thereof.

FIG. 7 is a back view of the decorative medical device.

Figure 8:
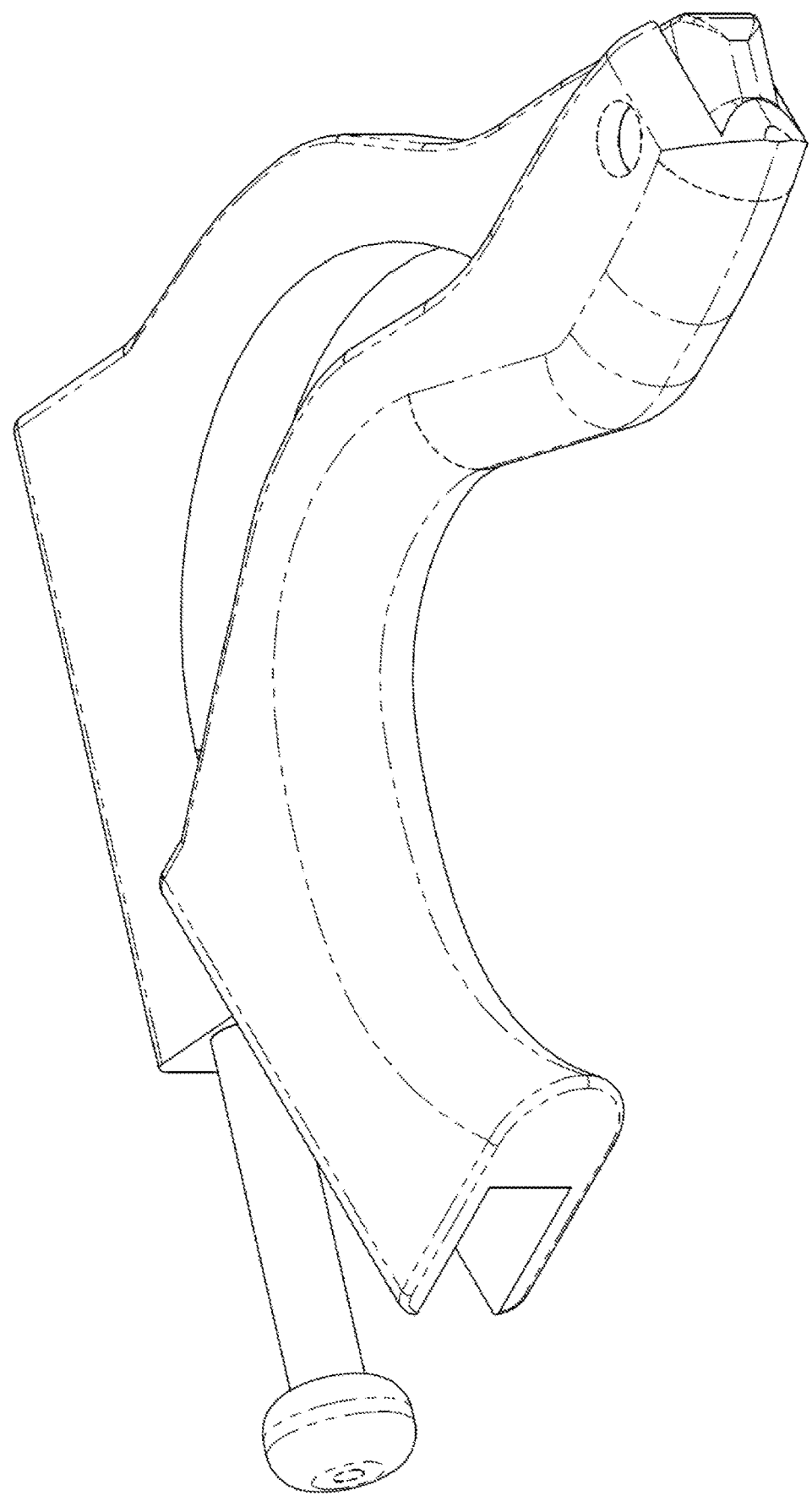
FIG. 8 is a perspective view of a medical device assembly.
Figure 9:
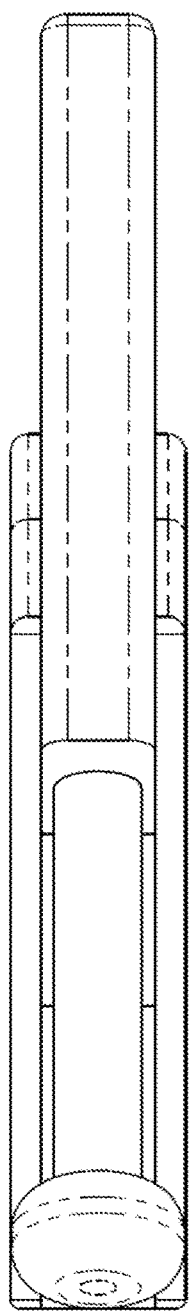
FIG. 9 is a top view thereof.
Figure 10:
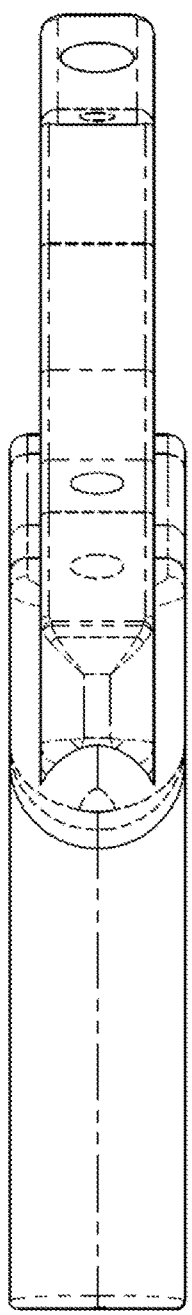
FIG. 10 is a bottom view thereof.
Figure 11:
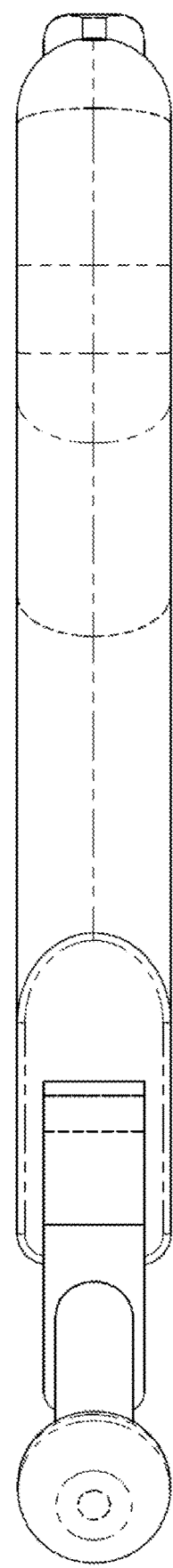
FIG. 11 is a left-side view thereof.
Figure 12:
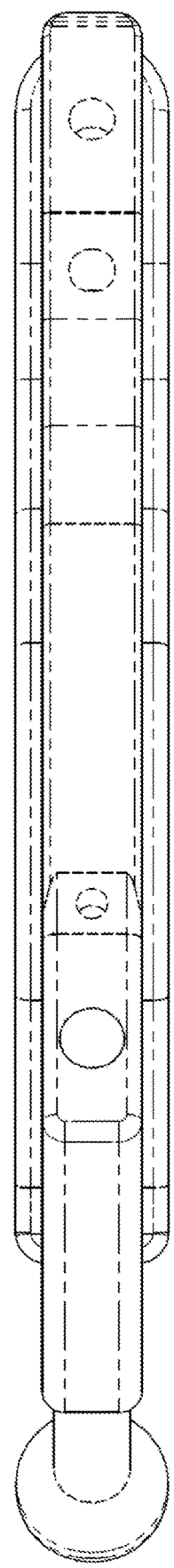
FIG. 12 is a right-side view thereof.
Figure 13:
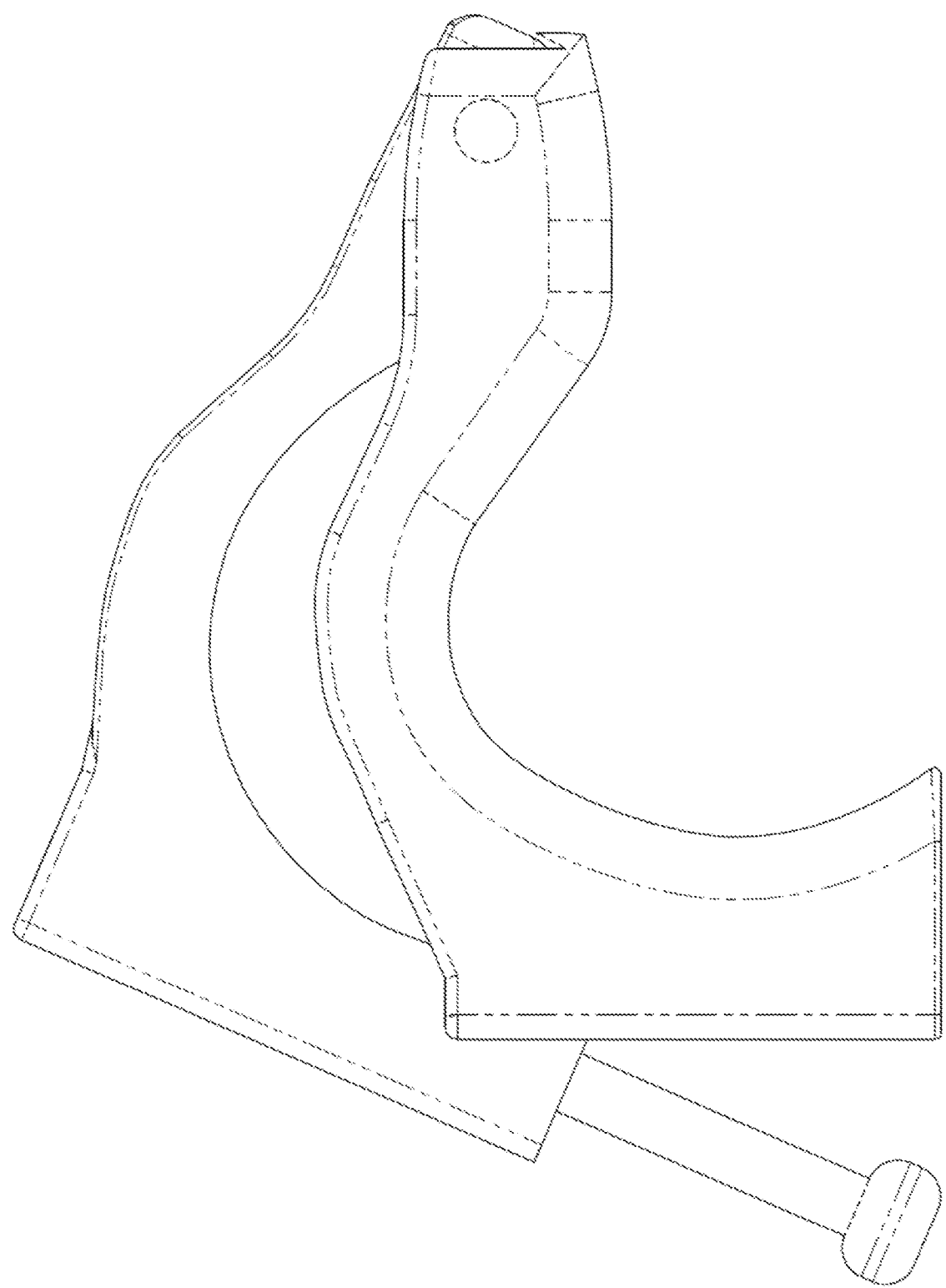
FIG. 13 is a front view thereof.

FIG. 8 is a perspective view of a medical device assembly;

FIG. 9 is a top view thereof;

FIG. 10 is a bottom view thereof;

FIG. 11 is a left-side view thereof;

FIG. 12 is a right-side view thereof;

FIG. 13 is a front view thereof; and

Figure 14:
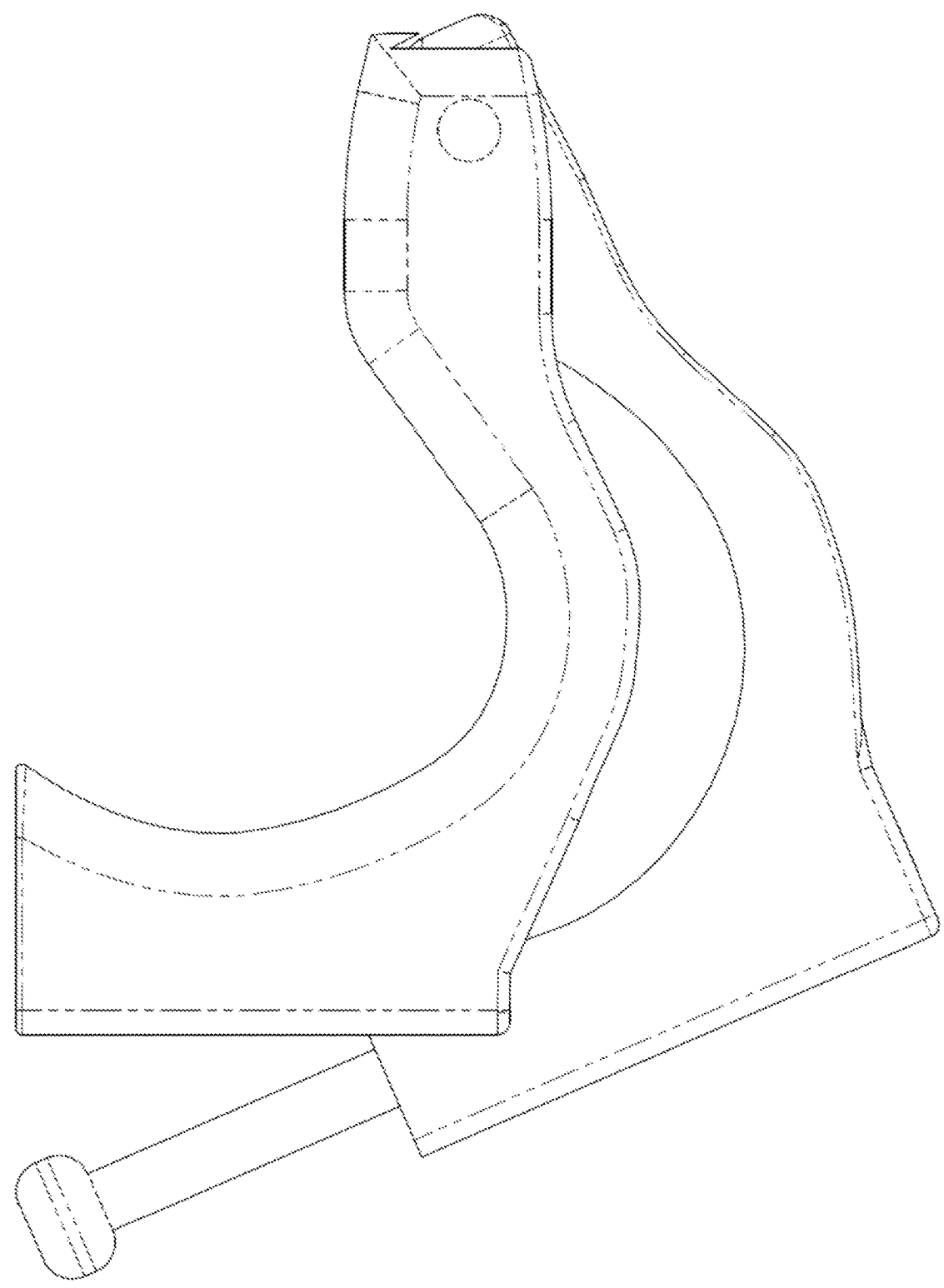
FIG. 14 is a back view thereof.

FIG. 14 is a back view thereof.

Figure 15A:
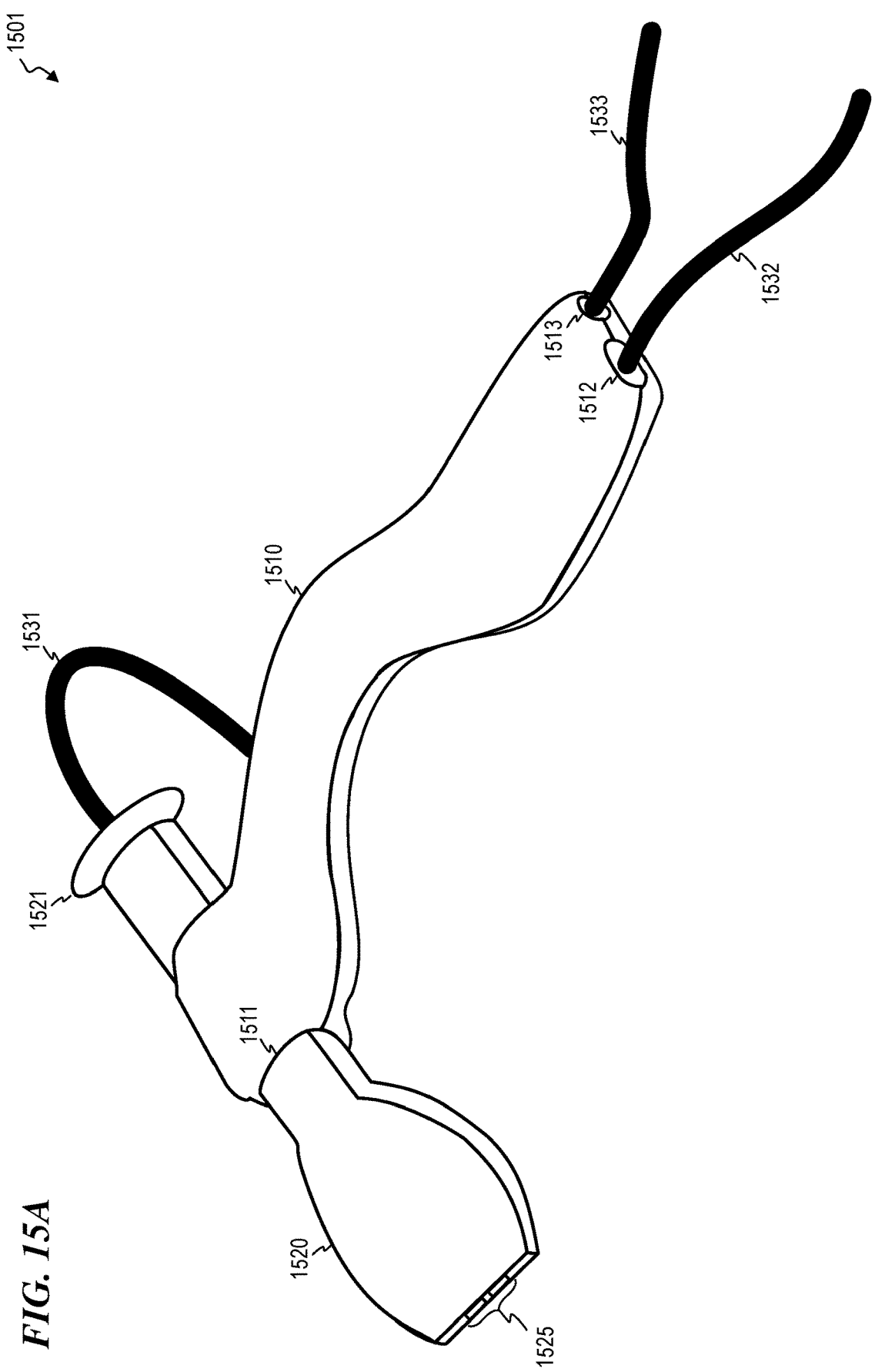
FIG. 15A is a perspective view of a cable-holder system 1501, according to some embodiments of the present invention.

FIG. 15A is a perspective view of a cable-holder system 1501, according to some embodiments of the present invention. In some embodiments, system 1501 includes a base portion 1510 configured to fit around an ear of a patient and a moveable portion 1520 (sometimes referred to herein as a "slider") coupled to the base portion 1510 at the "top" of base portion 1510 (i.e., the part of base portion 1510 located toward the top of the ear when base portion 1510 is in place on the patient). In some embodiments, slider 1520 includes an electrical connector 1525 configured to electrically couple to one or more stimulators located on the patient (e.g., electrodes, light emitters, magnetic-pulse sources, and/or heat sources located around the eye of the patient). In some embodiments, slider 1520 fits inside a hollow section 1511 of base portion 1520 such that slider 1520 can be moved to a plurality of horizontal positions relative to base portion 1510 in order to provide a patient-head-size-adjustment mechanism. In some such embodiments, the desired horizontal position of slider 1520 is selected based on the distance between the electrical connector 1525 and the electrical connection of the patient's stimulators, which allows system 1501 to fit a plurality of patient head sizes. In some embodiments, slider 1520 includes a flange 1521 that prevents slider 1520 from being pulled all the way through hollow section 1511 of base portion 1510. In some embodiments, base portion 1510 and slider 1520 are made from polymers (e.g., injection-molded polymers, 3D-printed polymers, and the like), metals, carbon fiber, and/or any other suitable material. In some embodiments, cable-holder system 1501 is reusable over a plurality of therapy sessions. For example, in some embodiments, cable-holder system 1501 is covered by a sanitizing film that is disposed after each use.

In some embodiments, electrical connector 1525 is electrically coupled to cable/electrical conduit 1531, which exits slider 1520 near flange 1521 and then passes into the body of base portion 1510. In some embodiments, base portion 1510 includes cable-exit ports 1512 and 1513. In some embodiments, cables/wires 1532 and 1533 exit base portion 1510 via cable-exit ports 1512 and 1513, respectively. In some embodiments, cables/wires 1532 and 1533 provide electrical connections to other electronic devices associated with a stimulation-treatment system such as ground electrodes, a second cable-holder system 1501 located on the other ear of the patient, and/or a therapy controller. In some embodiments, a therapy controller is affixed to the temple of the patient and operatively coupled to stimulators on a first side of the therapy controller and to cable-holder system 1501 on a second side of the therapy controller. In some embodiments, a therapy controller is contained within base portion 1510 (or is affixed to an outer surface of base portion 1510) and cable-holder system 1501 provides a device for physically supporting the connections between stimulators located on the patient and the therapy controller (in some such embodiments, cable-holder system 1501 includes a therapy controller within base portion 1510 and the therapy controller is operatively coupled (via electrical connection 1525 and cable/wires 1531, 1532, and/or 1533) to one or more electrode stimulators located around the eye of the patient and to one or more ground electrodes located on the head of the patient).

In some embodiments, cable-holder system 1501 (and/or a therapy controller located within or on cable-holder system 1501) includes wireless communication electronics that allow system 1501 to wirelessly communicate with a mobile device (e.g., a smart phone), base station (e.g., a computer laptop), and/or other systems 1501 such as a second system 1501 located on the second ear of the patient. In some such embodiments, system 1501 is configured to wirelessly communicate using Bluetooth®, near-field communications (NFC), cellular networks (e.g., Global System for Mobile Communications (GSM)), Wi-Fi, and/or any other suitable wireless communication protocols/standards. In some embodiments, a respective system 1501 is located on each ear of a patient and is operatively coupled to a corresponding eye stimulator, and the respective systems 1501 communicate with each other (wirelessly or via a wired connection) to provide sequential or simultaneous eye stimulation to the patient.

In some embodiments, cable-holder system 1501 (and/or a therapy controller located within or on cable-holder system

1501) provides a touch pad or touch screen that allows the patient or other person (e.g., a medical professional) to adjust the stimulation level provided by the stimulators operatively coupled to system 1501. In some embodiments, system 1501 and/or a therapy controller coupled to system 1501 also includes audio electronics and light emitters configured to provide audio/visual cues to indicate progress and/or status of stimulation treatments provided by stimulators operatively coupled to system 1501.

Figure 15B:
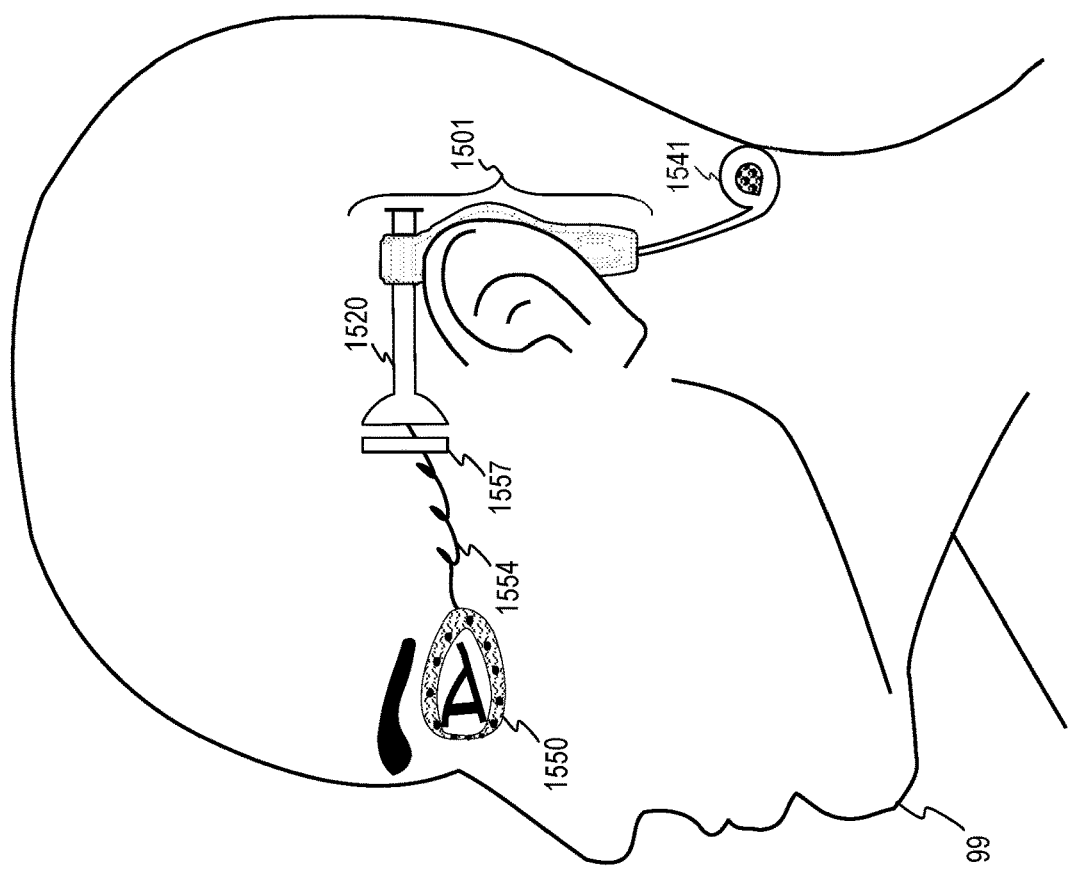
FIG. 15B is a perspective view of a stimulation-therapy system 1502, according to some embodiments of the present invention.

FIG. 15B is a perspective view of a stimulation-therapy system 1502, according to some embodiments of the present invention. In some embodiments, slider 1520 of system 1502 is coupled to an electrical conductor 1554 via an electrical connector 1557, and the electrical conductor 1554 is operatively coupled to an eye stimulator 1550 (e.g., in some embodiments, eye stimulator 1550 includes one or more stimulation electrodes configured to provide a therapeutic level of electrical stimulation to the eye of patient 99). In some embodiments, system 1502 is also operatively coupled to one or more ground electrodes 1541 located on the backside of the head of patient 99 (in some embodiments, ground electrodes 1541 are placed in contact with skin on the neck of patient 99; in some embodiments, ground electrodes 1541 are placed in contact with skin in any other suitable location on patient 99). In some embodiments, a duplicate of system 1502 is located on the other side of patient 99 and is configured to communicate (wirelessly or via a wired connection) with system 1502. In some embodiments, system 1502 and its duplicate on the other side of patient 99 each include a respective therapy controller coupled to a corresponding cable-holder system 1501 (in some such embodiments, each respective therapy controller is contained within a corresponding cable-holder system 1501). In other embodiments, system 1502 and its duplicate are controlled by a single therapy controller coupled to one of the respective cable-holder systems 1501.

Figure 15C:
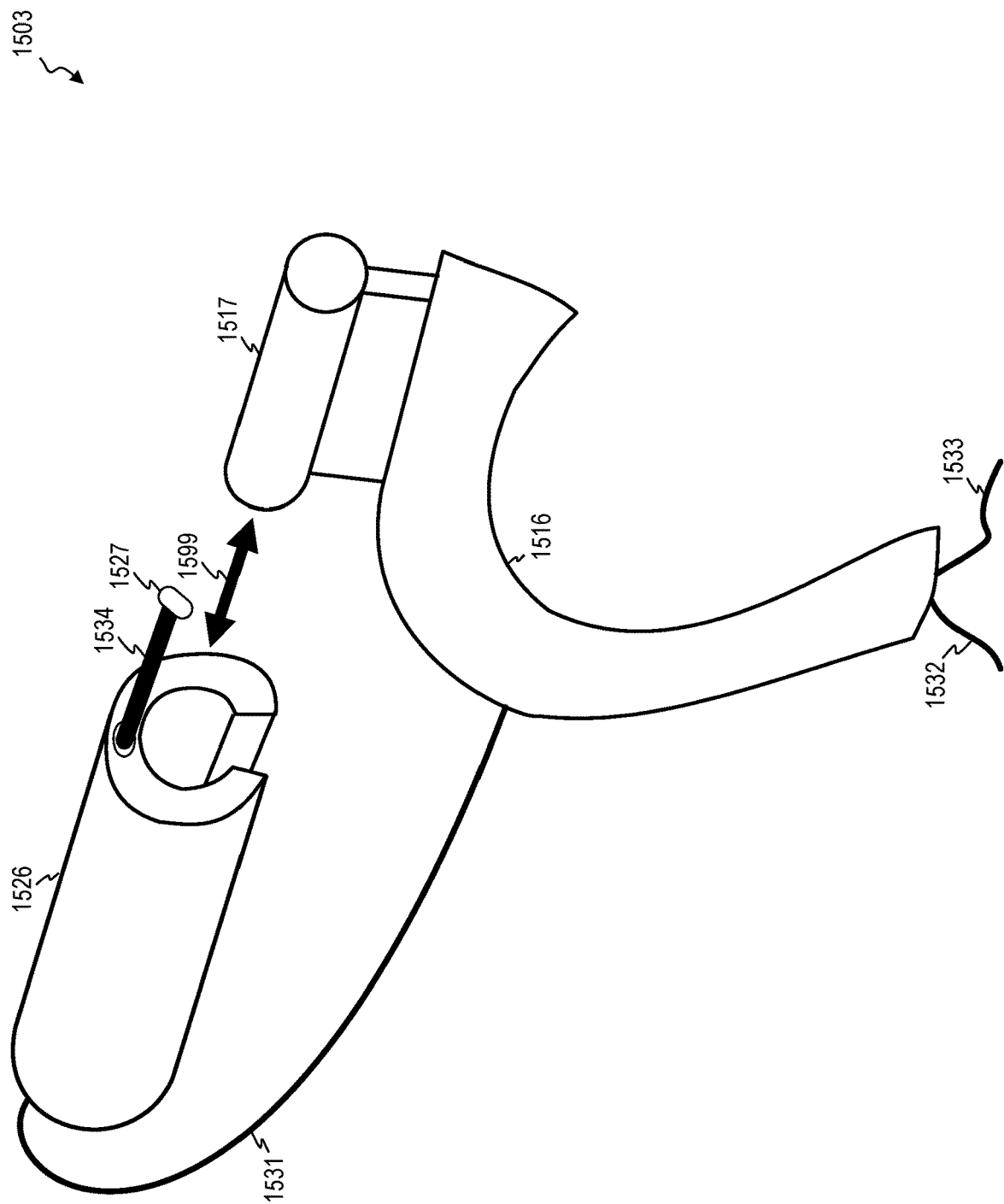
FIG. 15C is a perspective view of a cable-holder system 1503, according to some embodiments of the present invention.

FIG. 15C is a perspective view of a cable-holder system 1503, according to some embodiments of the present invention. In some embodiments, system 1503 is substantially similar to system 1501 except that base portion 1516 includes a top portion 1517 that slider 1526 slides over (in the direction of arrow 1599), rather than the slider moving through a hollow portion of the base portion as shown in FIG. 15A. In some embodiments, slider 1526 includes an extension 1534 having an electrical connection 1527 (e.g., a USB connector or other suitable electrical connector) configured to electrically couple to one or more stimulators located on the patient (e.g., electrodes, light emitters, magnetic-pulse sources, and/or heat sources located around the eye of the patient). In some embodiments (not shown), electrical connection 1527 is coupled directly to slider 1526 and there is no extension 1534.

Figures 1, 16A:
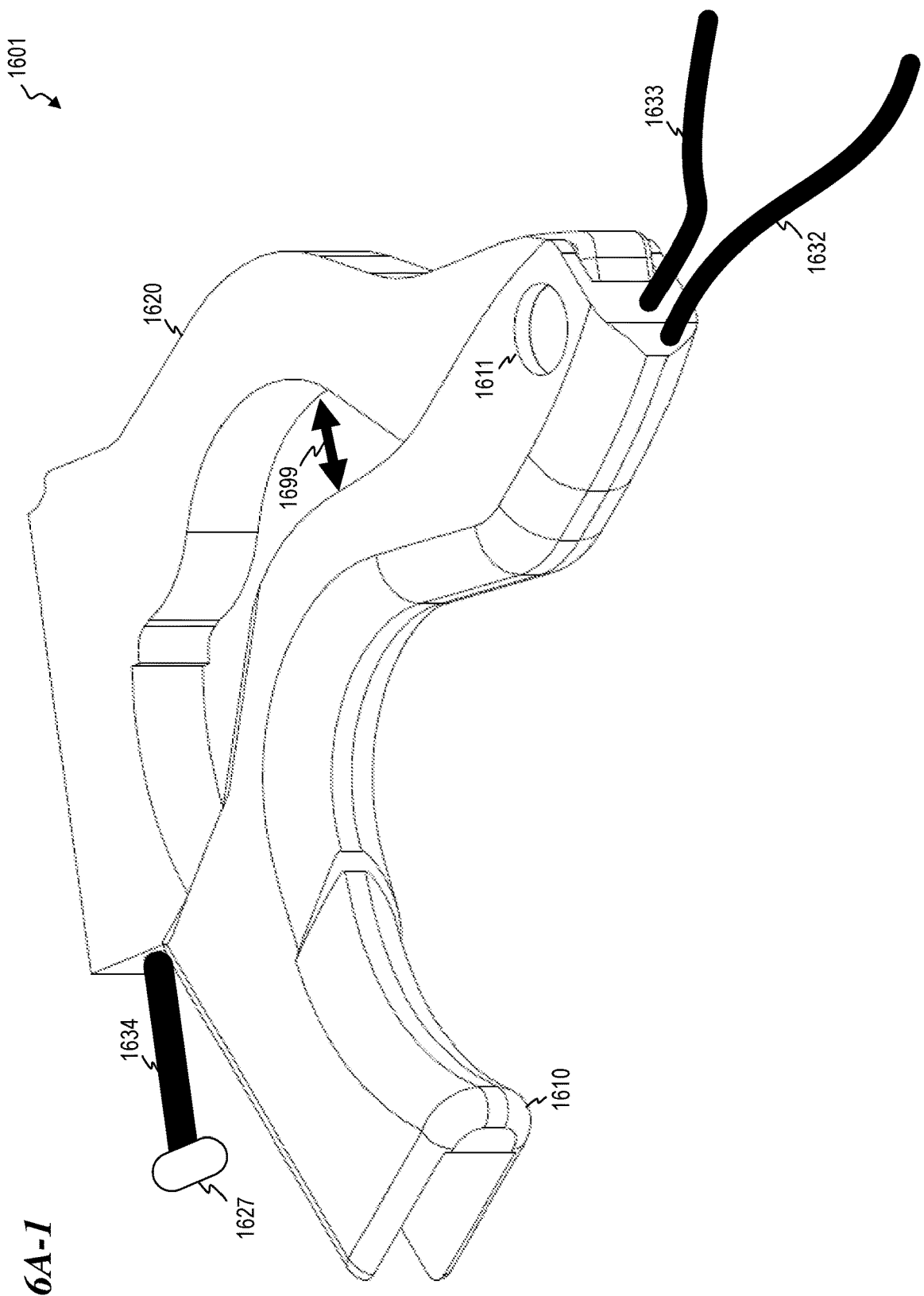
Figures 2, 16A:
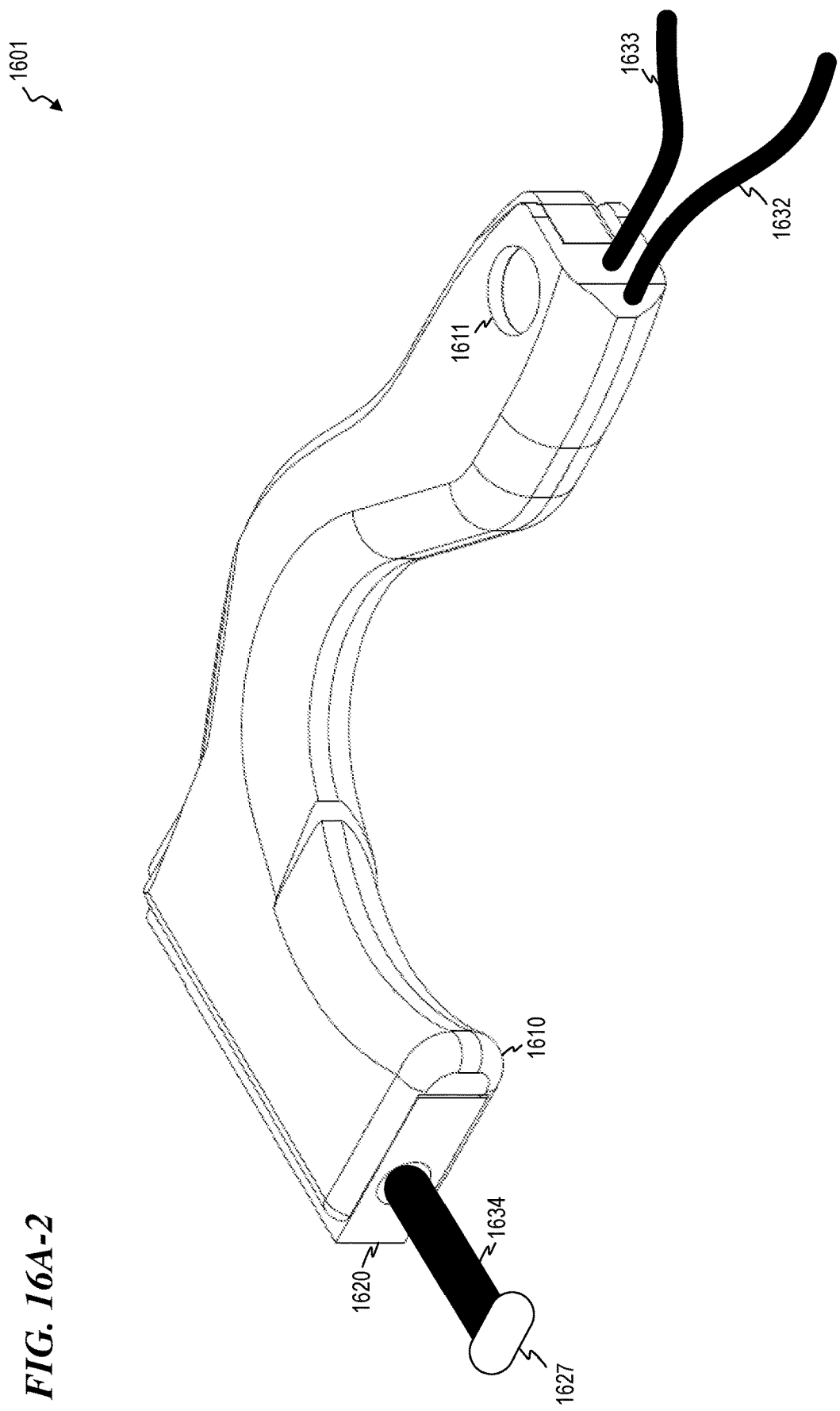

FIG. 16A-1 is a perspective view of a cable-holder system 1601, according to some embodiments of the present invention. In some embodiments, cable-holder system 1601 is similar to cable-holder system 1501 except that the patient-head-size-adjustment mechanism on system 1601 involves a rotational movement rather than a horizontal sliding movement. In some embodiments, cable-holder system 1601 includes a base portion 1610 coupled to cables/wires 1632 and 1633 and configured to fit around the ear of a patient, a moveable portion 1620 coupled to a flexible extension 1634 having an electrical connection 1627 (e.g., a USB connection or other suitable electrical connection), and a rotation mechanism 1611 (e.g., in some embodiments, a pin that forms a pivot point between base portion 1610 and moveable portion 1620) operatively coupled to base portion 1610 and movable portion 1620. In some embodiments (not shown), electrical connection 1627 is coupled directly to moveable portion 1620 and there is no flexible extension 1634. In some embodiments, the distance between the electrical connection 1627 and the electrical connection of the patient's stimulators is adjusted by rotating moveable portion 1620 around rotation mechanism 1611 such that moveable portion 1620 moves in the direction of arrow 1699 and such that electrical connection 1627 is moved closer or farther away from the patient's stimulators.

FIG. 16A-2 is a perspective view of a cable-holder system 1601 showing moveable portion 1620 rotated such that cable/wire 1631 is fully extended away from system 1601, according to some embodiments of the present invention.

Figure 16B:
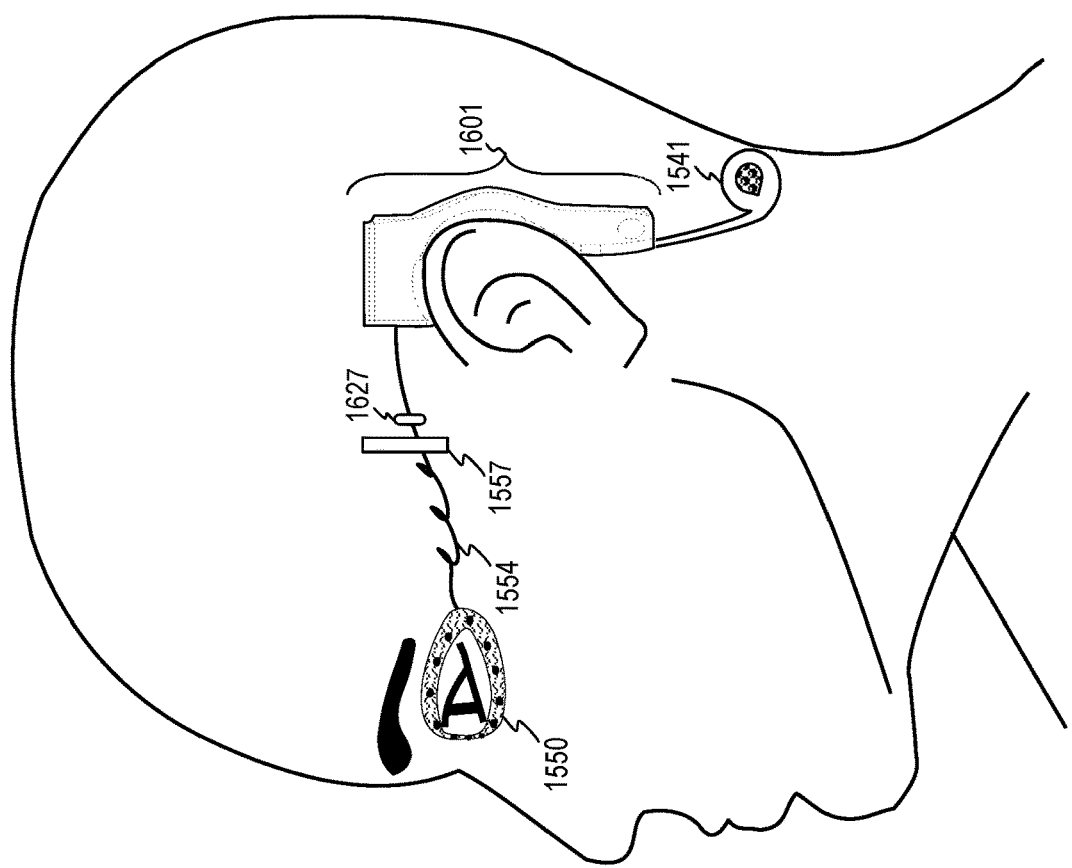
FIG. 16B is a perspective view of a stimulation-therapy system 1602, according to some embodiments of the present invention.

FIG. 16B is a perspective view of a stimulation-therapy system 1602, according to some embodiments of the present invention. In some embodiments, system 1602 is substantially similar to system 1502 of FIG. 15B except that cable-holder system 1501 is replaced by cable-holder system 1601.

Figure 17A:
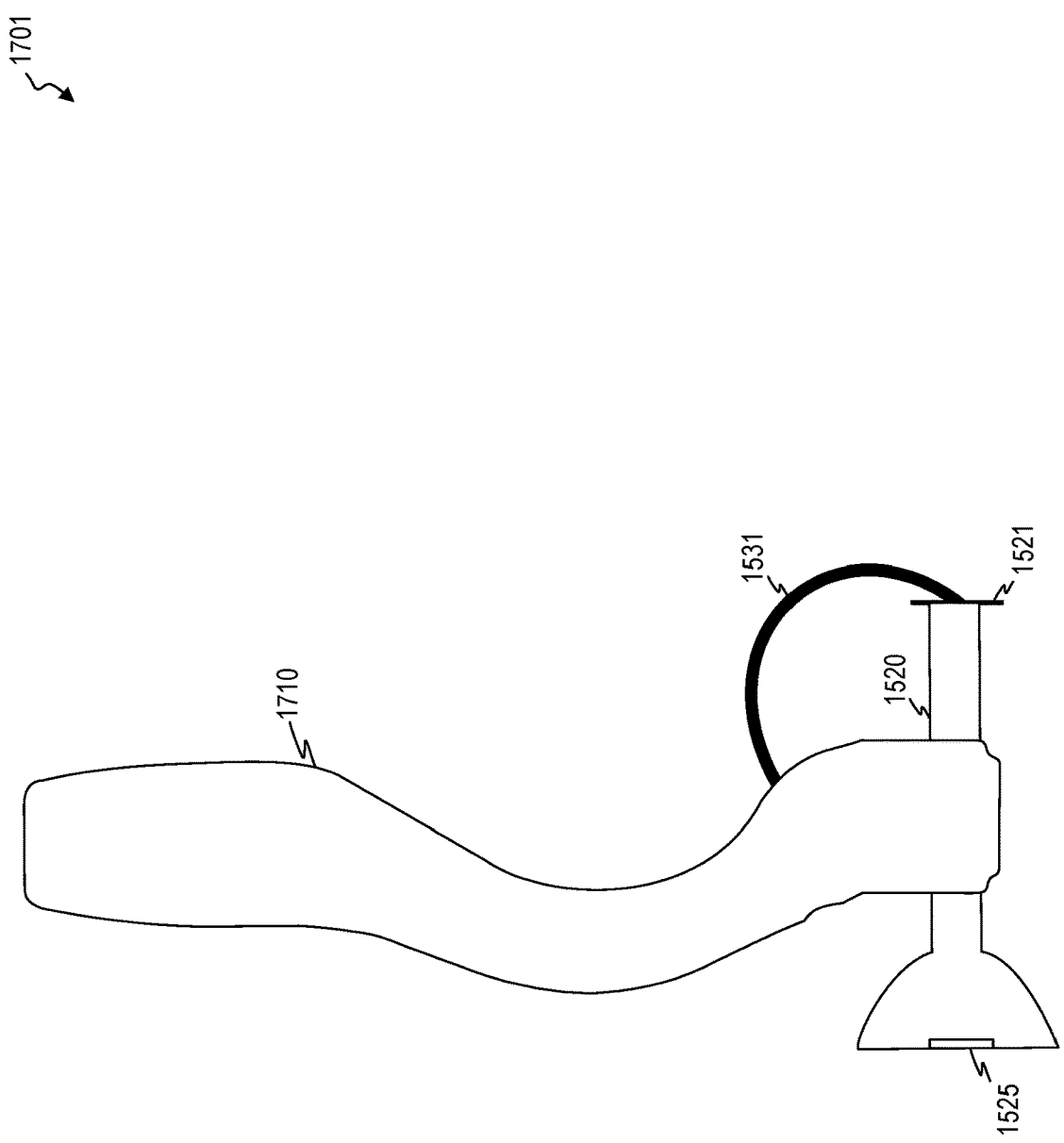
FIG. 17A is a perspective view of a cable-holder system 1701, according to some embodiments of the present invention.

FIG. 17A is a perspective view of a cable-holder system 1701, according to some embodiments of the present invention. In some embodiments, system 1701 is substantially similar to system 1501 of FIG. 15A except that base portion 1510 is replaced with head connector 1710 that is configured to be placed at least partially around the head of the patient instead of at least partially around the ear of the patient.

Figure 17B:
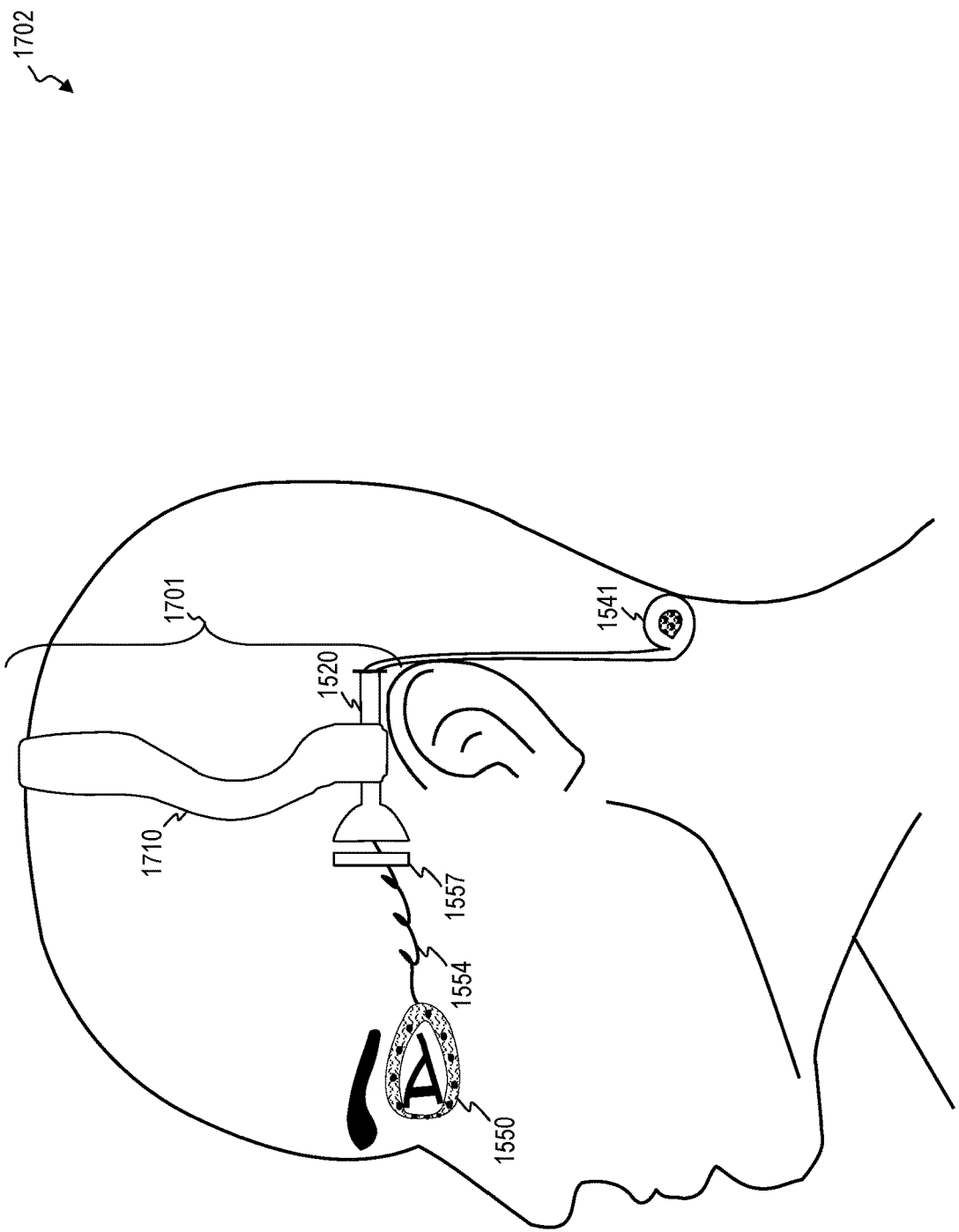
FIG. 17B is a perspective view of a stimulation-therapy system 1702, according to some embodiments of the present invention.

FIG. 17B is a perspective view of a stimulation-therapy system 1502, according to some embodiments of the present invention. In some embodiments, head connector 1710 comprises a strap or band that fits around the top of the patient's head such that a respective slider 1520 is coupled to each end of head connector 1710 just above a corresponding ear of the patient 99. In some embodiments, head connector is configured to fit tightly around the patient's head such that cable-holder system 1701 is held in place during use.

Figures 18A, 18B:
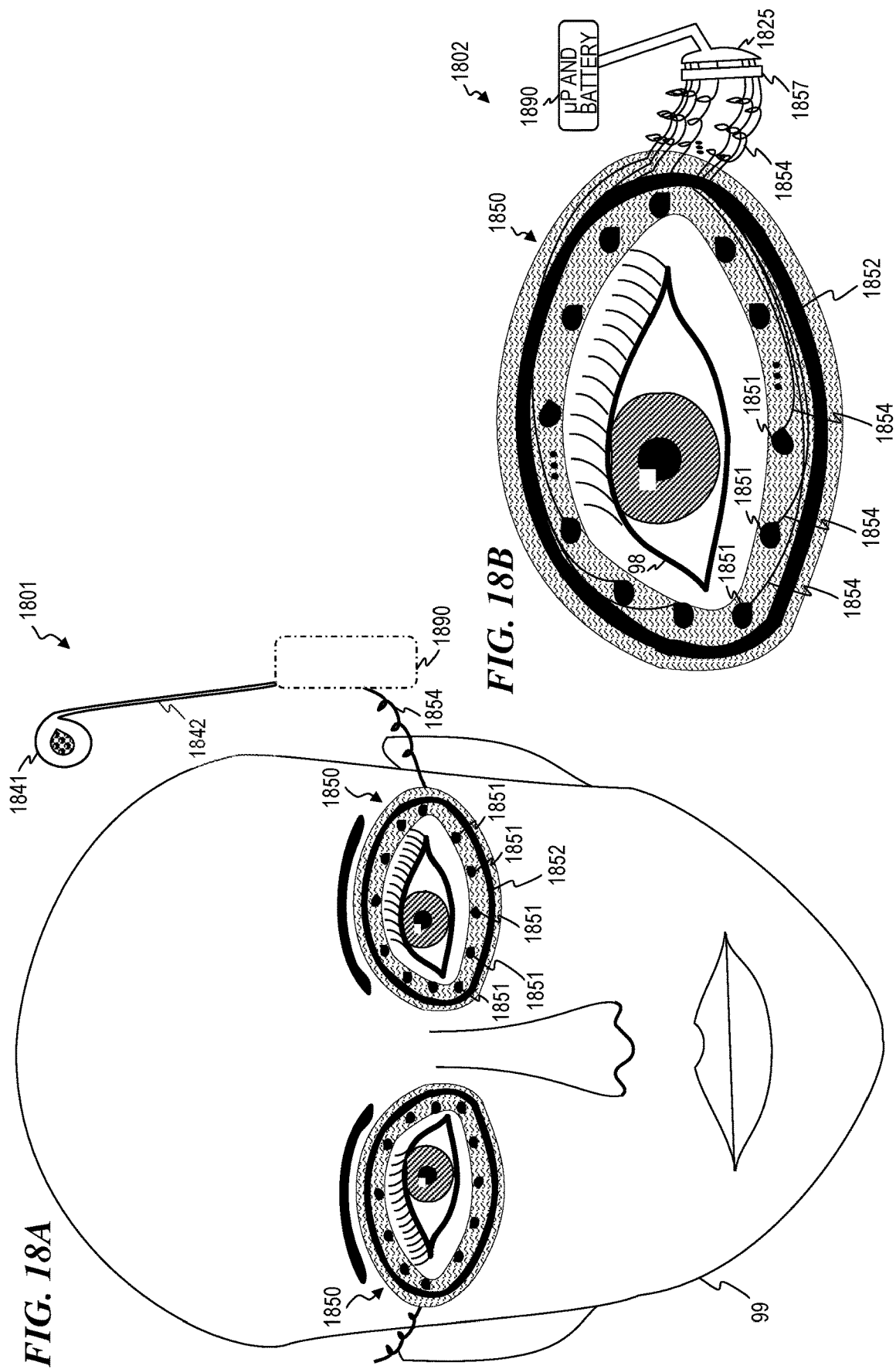
FIG. 18A is a schematic front-view diagram of a therapy-appliance system 1801 having two substrates 1850 positioned around the left and right eyes, respectively, of a person 99, according to some embodiments of the present invention.
FIG. 18B is a front view of a system 1802 showing a therapy-appliance substrate 1850 positioned around a person's eye 98, according to some embodiments of the present invention.

FIG. 18A is a schematic front-view diagram of a therapy-appliance system 1801 having two substrates 1850 positioned around the left and right eyes, respectively, of a person 99, showing exemplary positions of electrodes 1851, a ring electrode 1852, and connections to treatment-control apparatus 1890, according to some embodiments of the present invention. In some embodiments, each substrate 1850 is fit within the respective eye's orbit laying over the outer portions of the globe of the eye. In some embodiments, for each substrate 1850, each electrode 1851 of a plurality of individually activatable electrodes 1851 is coated with an electrically conductive gel and surrounded by an electrically insulating adhesive, in order that when an electrical signal is applied to a first selected electrode 1851, the current goes into the tissue of the patient 99 only under that first electrode (and, in some embodiments, one or more other electrodes 1851) when the signal from treatment-control apparatus 1890 is active to the first electrode (and the one or more other electrodes 1851 if those electrodes are also driven at that time). In some embodiments, the area of tissue under each one of a plurality of electrodes 1851 is between about 1 mm$^2$ and about 50 mm$^2$ (e.g., each electrode having electrical contact to skin in a square of about 1 mm by 1 mm to a square of about 7 mm by 7 mm, or a circle having a diameter of about 1.125 mm to about 8 mm). In some embodiments, the area of tissue under each one of a plurality of electrodes 1851 is any other suitable size.

In some embodiments, each therapy-appliance substrate 1850 includes electrical conductors 1854 electrically coupled to treatment-control apparatus 1890. In some embodiments, treatment-control apparatus 1890 is located locally (e.g., in a battery operated unit that is carried by person 99, such as in a shirt pocket or head-mounted elastic band or in/on an cable-holder like, for example, cable-holder system 1501 of FIGS. 15A-15B), while in other embodiments, treatment-control apparatus 1890 is attached to or part of a computer-controlled apparatus such as a laptop personal computer, a tablet computer, a desktop computer or the like. Therapy signals from the treatment-control apparatus 1890 are carried by the connection wire bundle 1854 to electrodes 1851, which deliver the current load to the patient's tissue.

In some embodiments, system 1801 includes one or more electrodes 1841, which are placed in contact with skin on patient 99 (e.g., in some embodiments, one or more electrodes 1841 are placed in contact with skin on the backside of the head of patient 99; in some embodiments, one or more electrodes are placed in contact with skin on the neck of patient 99; in some embodiments, one or more electrodes 1841 are placed in contact with skin in any other suitable location on patient 99), and attached to the main device (treatment-control apparatus 1890) by conductor (e.g., in some embodiments, wire) 1842. In some embodiments, therapeutic electrical-stimulation pulses are applied to the electrodes 1851 and/or ring electrode 1852 on therapy substrates 1850 surrounding each eye, wherein the return path (i.e., the ground signal) is provided through electrodes 1841.

FIG. 18B is a front view of a system 1802 showing a therapy-appliance substrate 1850 positioned around a person's eye 98, showing exemplary position of electrodes and connections to treatment-control apparatus 1890, according to some embodiments of the present invention. In some embodiments, treatment-control apparatus 1890 includes a microprocessor (µP) operated by a battery, and optionally is controlled and/or programmed by a nearby laptop personal computer, a tablet computer, a desktop computer or the like. In some embodiments, substrate 1850 includes electrical conductors 1854 electrically coupled to an electrical connector 1857 that plugs into or otherwise electrically connects to a corresponding connector 1825 on treatment-control apparatus 1890.

In some embodiments, ring electrode 1852, when activated by treatment-control apparatus 1890, provides electrical stimulation that occurs around the entire perimeter of ring electrode 1852 such that the entire perimeter of eye 98 receives the electrical stimulation. In other embodiments, ring electrode 1852 is configured to provide electrical stimulation to only selected locations along the perimeter of ring electrode 1852. In some embodiments, during a therapy session provided to eye 98, a first level of stimulation is provided by ring electrode 1852, and at least a second level of stimulation is provided at one or more selected electrodes 1851 located in one or more different locations around the perimeter of eye 98 (in some such embodiments, the first level of stimulation provided by ring electrode 1852 is provided simultaneously with the second level of stimulation provided by the one or more selected electrodes 1851; in other such embodiments, the second level of stimulation provided by the one or more selected electrodes 1851 occurs sequentially to the first level of stimulation provided by ring electrode 1852). In some embodiments, the first level of stimulation acts as a sub-threshold stimulation that primes the eye 98 such that actual electrical stimulation of eye 98 only occurs once the one or more selected electrodes 1851 deliver their electrical signal to eye 98. In some embodiments, ring electrode 1852 and one or more electrodes 1851 each provide the same level of electrical stimulation. In some embodiments, since electrodes 1851 are individually activatable, each electrode 1851 is capable of providing a different, selectable level of stimulation.

FIG. 19A is a schematic front-view diagram of a therapy-appliance system 1901 having two substrates 1950 positioned around the left and right eyes, respectively, of a person 99, showing a ring electrode 1952 and connections to treatment-control apparatus 1890, according to some embodiments of the present invention. In some embodiments, ring electrode 1952, when activated by treatment-control apparatus 1890, provides electrical stimulation that occurs around the entire perimeter of ring electrode 1952 such that the entire perimeter of eye 98 receives the electrical stimulation. In other embodiments, ring electrode 1952 is configured to provide electrical stimulation to only a selected location or selected locations along the perimeter of ring electrode 1952. The other various reference numbers in FIG. 19A are as described above for FIG. 18A.

FIG. 19B is a front view of a system 1902 showing a therapy-appliance substrate 1950 positioned around a person's eye 98, showing ring electrode 1952 and connections to treatment-control apparatus 1890, according to some embodiments of the present invention. The other various reference numbers in FIG. 19B are as described above for FIG. 18B.

Figure 20:
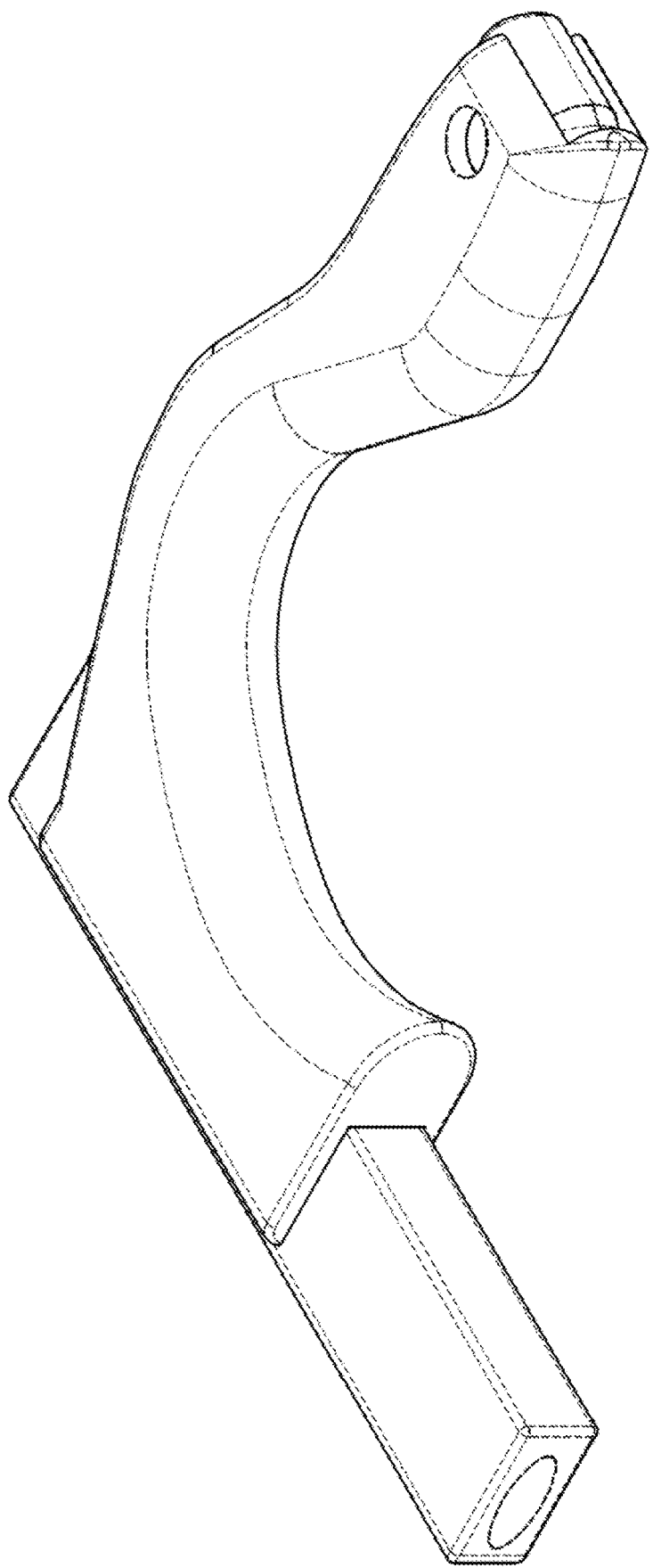
FIG. 20 is a first perspective view of a medical device apparatus 2001.

FIG. 20 is a first perspective view of a medical device apparatus 2001. In some embodiments, apparatus 2001 is functionally similar to cable-holder system 1601 except that apparatus 2001 does not include flexible extension 1634.

Figure 21:
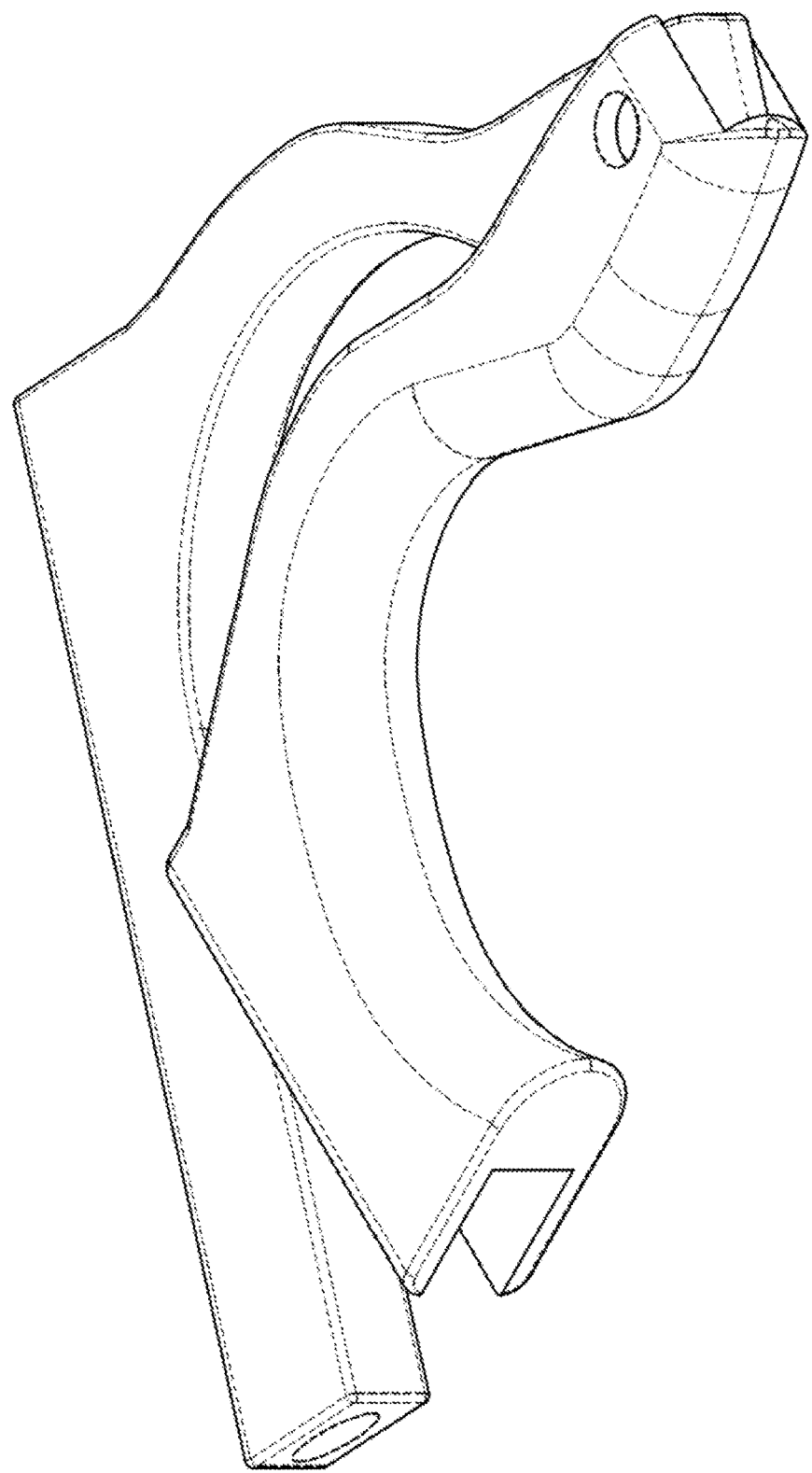
FIG. 21 is a second perspective view of apparatus 2001, showing the apparatus in a "rotated" position.

FIG. 21 is a second perspective view of apparatus 2001, showing the apparatus in a "rotated" position.

Figure 22:
FIG. 22 is a top view of apparatus 2001.

FIG. 22 is a top view of apparatus 2001.

Figure 23:
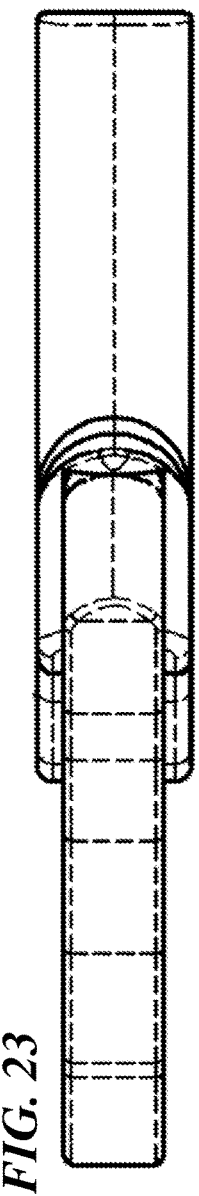
FIG. 23 is a bottom view of apparatus 2001.

FIG. 23 is a bottom of apparatus 2001.

Figure 24:
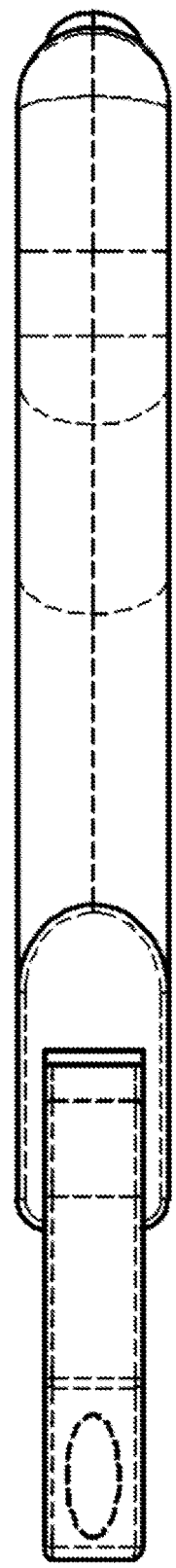
FIG. 24 is a left-side view of apparatus 2001.

FIG. 24 is a left-side view of apparatus 2001.

Figure 25:
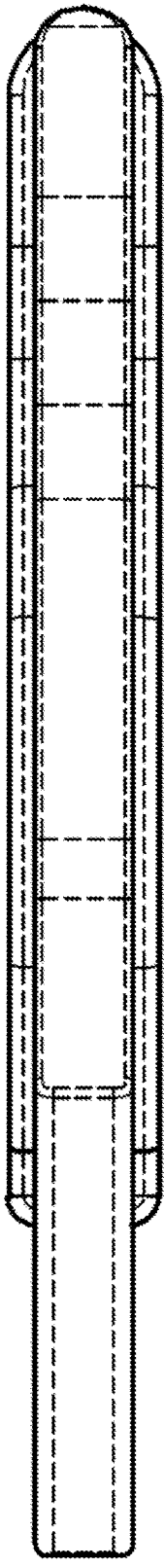
FIG. 25 is a right-side view of apparatus 2001.

FIG. 25 is a right-side view of apparatus 2001.

Figure 26:
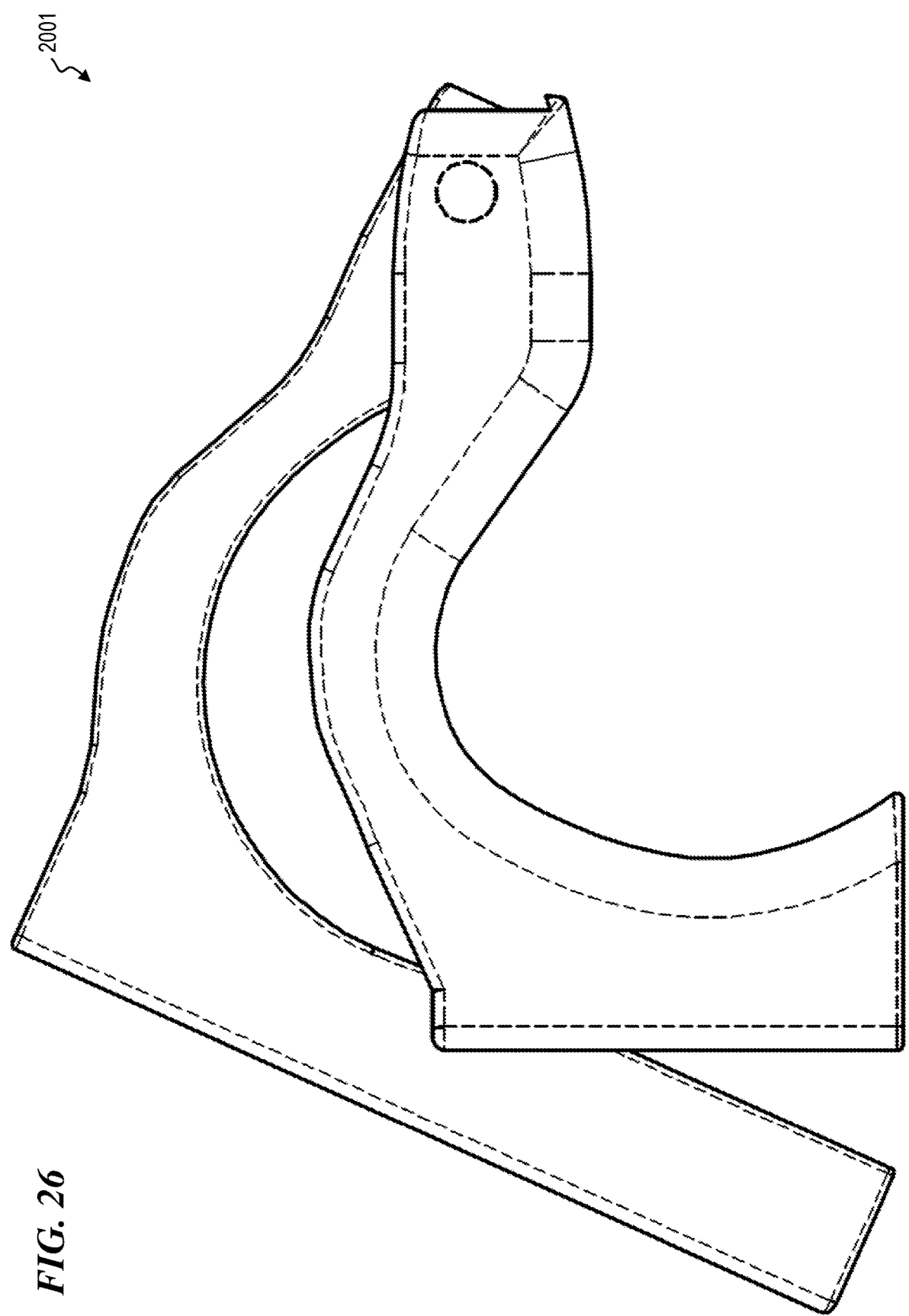
FIG. 26 is a front view of apparatus 2001.

FIG. 26 is a front view of apparatus 2001.

Figure 27:
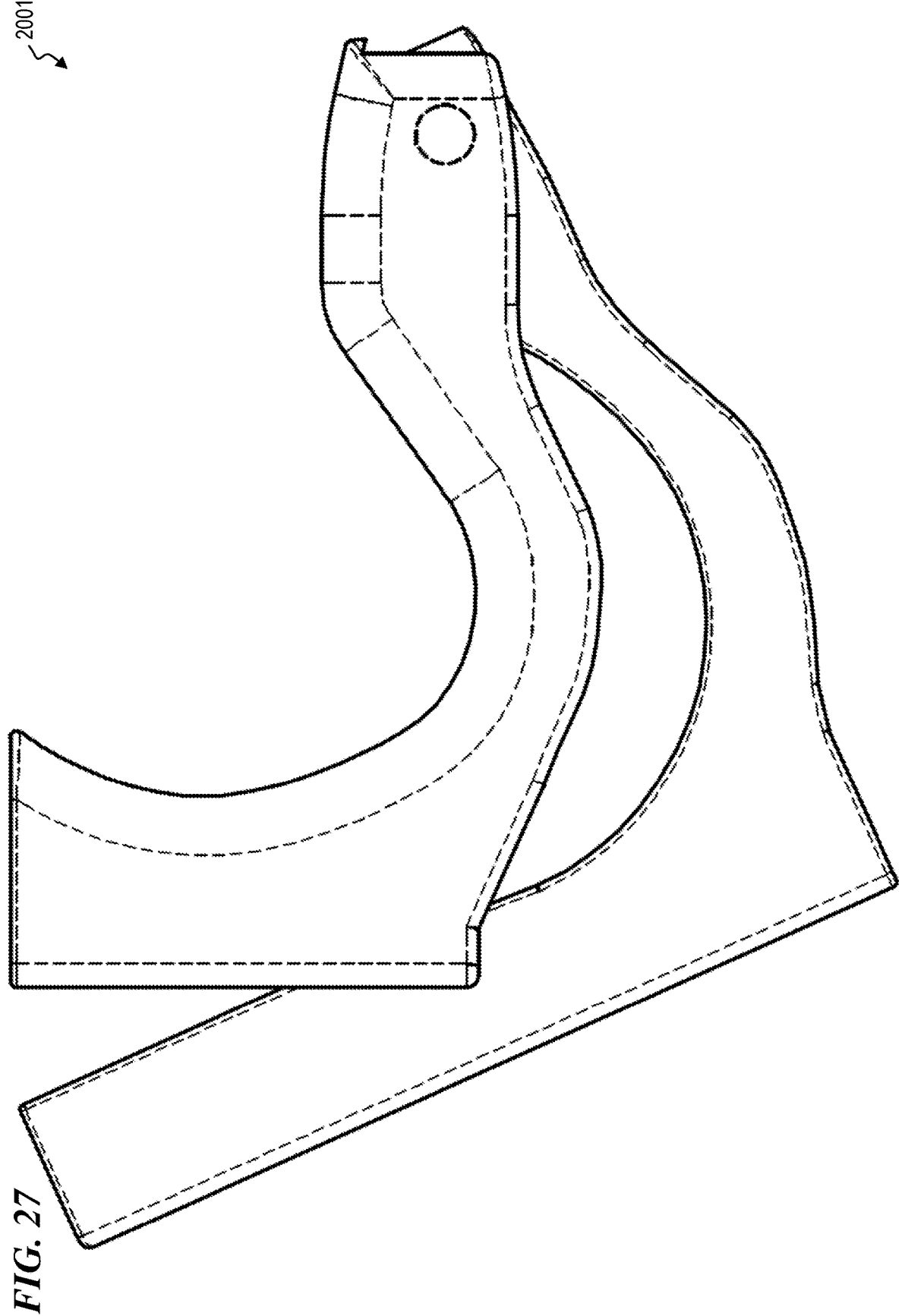
FIG. 27 is a back view of apparatus 2001.

FIG. 27 is a back view of apparatus 2001.

In some embodiments, the present invention provides a cable-holder system for physically supporting connections to a medical device used on a patient, the system including a first portion configured to be supported at the patient's head; a second portion moveably coupled to the first portion; and an electrical connector configured to electrically connect to the medical device, wherein the electrical connector is physically connected to the second portion. In some embodiments of the system, the first portion is configured to fit at least partially around a first ear of the patient. In some embodiments, the first portion is configured to be supported by a first ear of the patient. In some embodiments, the first portion is configured to wrap at least partially around the patient's head. In some embodiments, the first portion is configured to extend across a top portion of the patient's head.

In some embodiments of the system, the second portion is configured to adjustably slide between a plurality of horizontal positions relative to the first portion, wherein each of the plurality of horizontal positions is located at a respective distance from the medical device. In some embodiments, the second portion includes a rotation mechanism (e.g., a hinge) such that the second portion can be rotated relative to the first portion in order to change a distance between the electrical connector and the medical device. In some embodiments, the system further includes the medical device, wherein the medical device includes a plurality of electrodes configured to provide electrical stimulation to the patient; and a therapy controller operatively coupled to the plurality of electrodes, wherein the therapy controller is attached to the first portion of the cable-holder system.

In some embodiments, the system further includes a signal cable extending to the first portion from the electrical connector of the second portion; and a controller located in the second portion operatively coupled to the signal cable. In some embodiments, the system further includes a controller located separately from the second portion; and a signal cable operatively connecting the controller to the electrical connector of the second portion.

In some embodiments, the second portion is configured to adjustably slide between a plurality of horizontal positions relative to the first portion, the system further including the medical device, wherein the medical device includes a ring electrode that encircles an eye of the patient and is configured to provide electrical stimulation to the eye of the patient, wherein each of the plurality of horizontal positions is located at a respective distance from the medical device; a ground electrode; and a therapy controller operatively coupled to the ring electrode and the ground electrode, wherein the therapy controller is attached to the first portion of the cable-holder system, and wherein the therapy controller is configured to control electrical stimulation provided by the ring electrode.

In some embodiments, the system further includes the medical device, wherein the medical device includes a ring electrode that encircles an eye of the patient and a plurality of individually activated electrodes that surround the eye, wherein the ring electrode is configured to provide a first level of electrical stimulation to the eye and each of the plurality of individually activated electrodes is configured to provide at least a second level of electrical stimulation; a ground electrode; and a therapy controller operatively coupled to the ring electrode and the plurality of individually activated electrodes, wherein the therapy controller is attached to the first portion of the cable-holder system, and wherein the therapy controller is configured to control electrical stimulation provided by the ring electrode and the plurality of individually activated electrodes such that the first level of electrical stimulation is provided simultaneously (or sequentially) with the second level of electrical stimulation.

In some embodiments, the medical device includes a first stimulator located at least partially around a first eye of the patient and a second stimulator located at least partially around a second eye of the patient, wherein the electrical connector of the second portion is configured to electrically connect to the first stimulator, and wherein the first and second portions together form a first holder, the system further including a third portion configured to be supported at the patient's head; a fourth portion moveably coupled to the third portion; and an electrical connector configured to electrically connect to the second stimulator, wherein the electrical connector is physically connected to the fourth portion, wherein the third and fourth portions together form a second holder, and wherein the first and second holders include electronics such that the first and second holders are configured to wirelessly communicate with each other.

In some embodiments, the present invention provides a method for physically supporting connections to a medical device used on a patient, the method including providing a first cable-holder portion; providing a second cable-holder portion, wherein the second cable-holder portion includes an electrical connector; coupling the second cable-holder portion to the first cable-holder portion such that the second cable-holder portion can move relative to the first cable-holder portion; supporting the first cable-holder portion at the patient's head; adjusting a distance between the electrical connector and the medical device; and connecting the electrical connector of the second cable-holder portion to the medical device.

In some embodiments of the method, the supporting of the first cable-holder portion includes fitting the first cable-holder portion at least partially around a first ear of the patient. In some embodiments, the supporting of the first cable-holder portion includes extending the first cable-holder portion across a top section of the patient's head. In some embodiments, the adjusting of the distance between the electrical connector and the medical device includes sliding the second cable-holder portion to a selected horizontal position of a plurality of horizontal positions relative to the first cable-holder portion. In some embodiments, the adjusting of the distance between the electrical connector and the medical device includes rotating the second cable-holder portion to a selected rotational position of a plurality of rotational positions relative to the first cable-holder portion. In some embodiments, the method further includes providing a signal cable; extending the signal cable to the first cable-holder portion from the electrical connector of the second cable-holder portion; providing a controller located in the first cable-holder portion; and operatively coupling the controller to the signal cable.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," " "second," and "third," etc., are used merely as labels, and are not intended to impose numerical requirements on their objects.

What is claimed is:

1. A system comprising:
    an electrical stimulation device that includes:
        a first electrode substrate configured to encircle a first eye of a patient without obstructing vision from the first eye,
        a first ring electrode on the first electrode substrate, wherein the first ring electrode is configured to encircle the first eye of the patient without obstructing vision from the first eye and to provide electrical stimulation to the first eye, and
        a therapy controller operatively coupled to the first ring electrode and configured to control the electrical stimulation provided by the first ring electrode.

2. The system of claim 1, wherein the first ring electrode includes one or more electrical connections, the system further comprising:
    an electrical-conductor holder configured to be supported by a first ear of the patient and to provide a variable-position electrical-conductor connector configured to receive the one or more electrical connections of the first ring electrode at one of a plurality of locations between the first eye and the first ear of the patient.

3. The system of claim 1, wherein the electrical stimulation device further includes at least a first ground electrode operatively coupled to the therapy controller and configured to be placed in contact with skin of the patient in a location on the patient remote from the first eye configured to provide a return path for the electrical stimulation.

4. The system of claim 1, wherein the first ring electrode, when activated by the therapy controller, provides the electrical stimulation around an entire perimeter of the first ring electrode.

5. The system of claim 1, wherein the first ring electrode, when activated by the therapy controller, provides the electrical stimulation to one or more selected locations on the first ring electrode.

6. The system of claim 1, wherein the electrical stimulation device further includes:
a second electrode substrate configured to encircle a second eye of the patient, and
a second ring electrode on the second electrode substrate, wherein the second ring electrode is configured to encircle the second eye of the patient and provide electrical stimulation to the second eye, and wherein the therapy controller is further operatively coupled to the second ring electrode.

7. The system of claim 1, wherein the first eye includes a first orbit and a first globe, wherein the first electrode substrate is configured to fit within the first orbit of the first eye such that the first electrode substrate lays over outer portions of the first globe of the first eye.

8. A method for providing electrical stimulation to a patient, the method comprising:
providing a first electrode substrate, wherein the first electrode substrate includes a first ring electrode;
attaching the first electrode substrate to the patient's skin, wherein the attaching of the first electrode substrate includes encircling a first eye of the patient with the first electrode substrate and the first ring electrode without obstructing vision from the first eye; and
applying electrical stimulation to the first eye via the first ring electrode.

9. The method of claim 8, further comprising:
providing at least a first ground electrode; and
attaching the at least first ground electrode to the patient's skin, wherein the applying of the electrical stimulation includes controlling a therapeutic electrical current between the first ring electrode and the at least first ground electrode.

10. The method of claim 8, wherein the applying of the electrical stimulation includes generating the electrical stimulation around an entire perimeter of the first ring electrode.

11. The method of claim 8, wherein the applying of the electrical stimulation includes generating the electrical stimulation at one or more selected locations on the first ring electrode.

12. The method of claim 8, further comprising:
providing a second electrode substrate, wherein the second electrode substrate includes a second ring electrode;
attaching the second electrode substrate to the patient's skin, wherein the attaching of the second electrode substrate includes encircling a second eye of the patient with the second electrode substrate and second ring electrode; and
applying electrical stimulation to the second eye via the second ring electrode.

13. The method of claim 8, wherein the first eye includes a first orbit and a first globe, wherein the attaching of the first electrode substrate includes fitting the first electrode substrate within the first orbit of the first eye such that the first electrode substrate lays over outer portions of the first globe of the first eye.

14. The method of claim 8, further comprising providing a microprocessor powered by a battery, wherein the applying of the electrical stimulation includes controlling generation of the electrical stimulation using the microprocessor.

15. A system comprising:
an electrical stimulation device that includes:
a first electrode substrate configured to encircle a first eye of a patient without covering the first eye,
a first ring electrode on the first electrode substrate, wherein the first ring electrode is configured to encircle the first eye of the patient without covering the first eye and to provide electrical stimulation to the first eye, and
a therapy controller operatively coupled to the first ring electrode and configured to control the electrical stimulation provided by the first ring electrode, wherein the therapy controller includes a microprocessor, wherein the electrical stimulation device further includes a first plurality of individually activatable electrodes on the first electrode substrate, wherein each of the first plurality of individually activatable electrodes is operatively coupled to the microprocessor of the therapy controller.

16. A system comprising:
an electrical stimulation device that includes:
a first electrode substrate configured to encircle a first eye of a patient without covering the first eye,
a first ring electrode on the first electrode substrate, wherein the first ring electrode is configured to encircle the first eye of the patient without covering the first eye and to provide electrical stimulation to the first eye,
a therapy controller operatively coupled to the first ring electrode and configured to control the electrical stimulation provided by the first ring electrode, and
a first plurality of individually activatable electrodes on the first electrode substrate, wherein the first plurality of individually activatable electrodes is operatively coupled to the therapy controller, wherein the electrical stimulation is formed by a combination of a first level of therapeutic stimulation provided by the first ring electrode and at least a second level of therapeutic stimulation provided by one or more of the first plurality of individually activatable electrodes.

17. A system comprising:
an electrical stimulation device that includes:
a first electrode substrate configured to encircle a first eye of a patient without covering the first eye,
a first ring electrode on the first electrode substrate, wherein the first ring electrode is configured to encircle the first eye of the patient without covering the first eye and to provide electrical stimulation to the first eye,
a therapy controller operatively coupled to the first ring electrode and configured to control the electrical stimulation provided by the first ring electrode, and
a first plurality of individually activatable electrodes on the first electrode substrate, wherein the first plurality of individually activatable electrodes is operatively coupled to the therapy controller, wherein the first plurality of individually activatable electrodes are located inside a perimeter formed by the first ring electrode, and wherein the electrical stimulation is formed by a combination of a first sub-threshold level of therapeutic stimulation provided by the first ring electrode and a simultaneous second level of therapeutic stimulation provided by one or more of the first plurality of individually activatable electrodes.

18. A method for providing electrical stimulation to a patient, the method comprising:
providing a first electrode substrate, wherein the first electrode substrate includes a first ring electrode;
attaching the first electrode substrate to the patient's skin, wherein the attaching of the first electrode substrate includes encircling a first eye of the patient with the first electrode substrate and the first ring electrode without covering the first eye;
applying electrical stimulation to the first eye via the first ring electrode; and
providing a first plurality of individually activatable electrodes on the first substrate, wherein the applying of the electrical stimulation includes generating a combination of a first level of therapeutic stimulation provided by the first ring electrode and at least a second level of therapeutic stimulation provided by one or more of the first plurality of individually activatable electrodes.

19. A method for providing electrical stimulation to a patient, the method comprising:
providing a first electrode substrate, wherein the first electrode substrate includes a first ring electrode;
attaching the first electrode substrate to the patient's skin, wherein the attaching of the first electrode substrate includes encircling a first eye of the patient with the first electrode substrate and the first ring electrode without covering the first eye;
applying electrical stimulation to the first eye via the first ring electrode; and
providing a first plurality of individually activatable electrodes on the first substrate, wherein the applying of the electrical stimulation includes generating a combination of a first sub-threshold level of therapeutic stimulation provided by the first ring electrode and a simultaneous second level of therapeutic stimulation provided by one or more of the first plurality of individually activatable electrodes.

20. A system for providing electrical stimulation to a first eye of a patient, the system comprising:
a first substrate;
means, on the first substrate, for applying a first sub-threshold level and a simultaneous second level of therapeutic electrical stimulation to the first eye of the patient; and
means for controlling the first sub-threshold level and the simultaneous second level of therapeutic electrical stimulation, wherein the means for controlling is electrically coupled to the means for applying.

\* \* \* \* \*